(12) United States Patent
Sato et al.

(10) Patent No.: US 12,274,781 B2
(45) Date of Patent: Apr. 15, 2025

(54) USE OF ENZYME-MODIFIED ISOQUERCITRIN

(71) Applicant: SAN-EI GEN F.F.I., INC., Toyonaka (JP)

(72) Inventors: Hiroyuki Sato, Toyonaka (JP); Makoto Nakauma, Toyonaka (JP); Akira Ikegami, Toyonaka (JP); Takahiro Funami, Toyonaka (JP); Hideyuki Orikoshi, Toyonaka (JP)

(73) Assignee: SAN-EI GEN F.F.I., INC., Osaka (JP)

( * ) Notice: Subject to any disclaimer, the term of this patent is extended or adjusted under 35 U.S.C. 154(b) by 1009 days.

(21) Appl. No.: 17/029,444

(22) Filed: Sep. 23, 2020

(65) Prior Publication Data

US 2021/0007980 A1    Jan. 14, 2021

Related U.S. Application Data

(62) Division of application No. 15/780,828, filed as application No. PCT/JP2016/085980 on Dec. 2, 2016, now abandoned.

(30) Foreign Application Priority Data

| Dec. 4, 2015 | (JP) | ................. | 2015-237874 |
| Dec. 4, 2015 | (JP) | ................. | 2015-237878 |

(51) Int. Cl.
| A61K 9/00 | (2006.01) |
| A23L 33/10 | (2016.01) |
| A61K 8/73 | (2006.01) |
| A61K 31/7048 | (2006.01) |
| A61K 47/36 | (2006.01) |
| A61P 1/02 | (2006.01) |
| A61Q 11/00 | (2006.01) |

(52) U.S. Cl.
CPC ............ *A61K 9/0056* (2013.01); *A23L 33/10* (2016.08); *A61K 8/73* (2013.01); *A61K 31/7048* (2013.01); *A61K 47/36* (2013.01); *A61P 1/02* (2018.01); *A61Q 11/00* (2013.01)

(58) Field of Classification Search
None
See application file for complete search history.

(56) References Cited

U.S. PATENT DOCUMENTS

| 5,496,558 | A | 3/1996 | Napolitano et al. |
| 5,580,880 | A | 12/1996 | Handa et al. |
| 7,033,606 | B1 * | 4/2006 | Besse .................. A61P 39/06 424/435 |
| 2003/0039706 | A1 | 2/2003 | Hirose et al. |
| 2006/0051472 | A1 | 3/2006 | Koda et al. |
| 2008/0182893 | A1 | 7/2008 | Nishizawa et al. |
| 2008/0187622 | A1 | 8/2008 | Moriwaki et al. |
| 2009/0143317 | A1 | 6/2009 | Ono et al. |
| 2011/0124577 | A1 * | 5/2011 | Taimatsu ........... A61K 31/7048 426/536 |
| 2014/0378547 | A1 | 12/2014 | Zielinski et al. |

FOREIGN PATENT DOCUMENTS

| EP | 1 669 462 A1 | 6/2006 |
| JP | H07-101856 A | 4/1995 |
| JP | H08-12575 A | 1/1996 |
| JP | H10-182392 A | 7/1998 |
| JP | H11-071253 A | 3/1999 |
| JP | 2001-064203 A | 3/2001 |
| JP | 2002-265375 A | 9/2002 |
| JP | 2003-040752 A | 2/2003 |
| JP | 2005-162633 A | 6/2005 |
| JP | 2009-531287 A | 9/2009 |
| JP | 2010-270045 A | 12/2010 |
| JP | 2012-085568 A | 5/2012 |
| JP | 2015-208241 A | 11/2015 |
| WO | 2007/092811 A2 | 8/2007 |
| WO | 2007/092811 A3 | 8/2007 |
| WO | 2009/060915 A1 | 5/2009 |

OTHER PUBLICATIONS

Office Action dated Aug. 6, 2021 from the China National Intellectual Property Administration in Chinese Application No. 201680080690.3.
Masamitsu Moriwaki et al., "Koketsuatsu Shizen Hassho Rat ni Okeru Koso Shori Isoquercitrin no Koka", Proceedings of the Annual Meeting of Japan Society for Bioscience, Biotechnology, and Agrochemistry, 2007 Nendo Taikai [Tokyo], Mar. 5, 2007, p. 281, 3B05p15.
International Search Report of PCT/JP2016/085980 dated Jan. 10, 2017 [PCT/ISA/210].
Extended European Search Report dated May 17, 2019 from the European Patent Office in European application No. 16870845.1.
Satoru Tamura et al., "Metabolic behavior of enzymatically modified isoquercitrin by α-amylase and gastric juices", Japanese Journal of Food Chemistry, 2005, pp. 152-156, vol. 12, No. 3.

(Continued)

*Primary Examiner* — Jennifer Chin
(74) *Attorney, Agent, or Firm* — Sughrue Mion, PLLC

(57) ABSTRACT

The present invention provides a salivator that is in a form for use in the mouth (a form for intraoral use), or in a form for use by oral administration (a form for oral administration). The salivator can be prepared by using enzymatically modified isoquercitrin, or a combination of enzyme-modified isoquercitrin and a thickening polysaccharide. The present invention further provides an additive that is useful for preparing an oral composition (a food or beverage, a pharmaceutical product for oral administration) (an additive for an oral composition) and that can impart at least one effect selected from the group consisting of a salivation-promoting effect, a deglutition-improving effect (swallowing-assisting effect), and a mastication-improving effect (chewing-assisting effect) to the oral composition. The additive can be prepared by using a combination of enzymatically modified isoquercitrin and a thickening polysaccharide.

11 Claims, 3 Drawing Sheets

(56) References Cited

OTHER PUBLICATIONS

Ayako Takahashi et al., "Evaluation of the Effects of Quercetin on Damaged Salivary Secretion", PLOS ONE, DOI:10.1371/journal.pone.0116008, Jan. 28, 2015, pp. 1-15.
Notice of Reasons for Refusal dated Sep. 8, 2020 from the Japanese Patent Office in Japanese Application No. 2016-235459.
Notice of Reasons for Refusal dated Sep. 8, 2020 from the Japanese Patent Office in Japanese Application No. 2016-235460.
Communication dated Jan. 8, 2021, from the China National Intellectual Property Administration in Chinese Application No. 201680080690.3.
Li Shaowen, "Ecological Biochemistry", Peking University Press, Nov. 2001,, pp. 225-226 (9 Pages Total).
Xu Bingyi et al., "The Decisive Role of Intestine and Stomach in Health", China Friendship Publishing Company, Aug. 2010, pp. 30-31 (5 Pages Total).
Mary Courtney Moore, "Pocket Guide to Nutritional Assessment and Care", People's Military Medical Press, Jan. 2009, p. 278 (5 pages total).

\* cited by examiner

USE OF ENZYME-MODIFIED ISOQUERCITRIN

CROSS REFERENCE TO RELATED APPLICATIONS

This application is a Divisional Application of U.S. application Ser. No. 15/780,828 filed Aug. 13, 2018, which is a National Stage of International Application No. PCT/JP2016/085980 filed on Dec. 2, 2016, which claims priority from Japanese Patent Application No. 2015-237874 filed on Dec. 4, 2015 and Japanese Patent Application No. 2015-237878 filed on Dec. 4, 2015, the contents of all of which are incorporated herein by references.

TECHNICAL FIELD

The present invention relates to the use of enzymatically modified isoquercitrin. More specifically, the present invention relates to the use of enzymatically modified isoquercitrin as a salivator, in particular, as a salivator in a form for use in the mouth (a form for intraoral use), or in a form for use by oral administration (a form for oral administration).

The present invention further relates to the use of enzymatically modified isoquercitrin as an additive for compositions for intraoral use or oral intake, such as foods and beverages or pharmaceutical products, so as to impart to the compositions at least one effect selected from the group consisting of a salivation-promoting effect, a deglutition-improving effect (swallowing-assisting effect) and a mastication-improving effect (chewing-assisting effect).

BACKGROUND ART

Saliva plays an important role, for example, in mouth functions and maintenance of the intraoral environment. Examples of mouth functions include the function of smoothening utterance and conversation, food intake function, and swallowing function. In particular, with respect to the food or beverage intake function and swallowing function, saliva is deeply involved in the action of forming an alimentary bolus, digestive activity by amylase secretion, and the action of maintaining taste sensation by solubilizing tastants and secreting carbonate dehydrogenase. Further, for maintenance of the intraoral environment, saliva is deeply involved in the self-cleaning effect in the mouth including the teeth, teeth remineralization effect, antibacterial effect, immunization effect, anti-inflammatory effect, and tissue-repair-promoting effect by growth factors etc.

However, the amount of saliva secretion is known to be reduced by various diseases, such as emotional and stress disorders, neurosis, organ dysfunction, encephalitis, tumors, cerebrovascular disorder, hypertension, Basedow's disease, and diabetes; side effects of medicine; radiation therapy; aging; etc. In particular, in the elderly, not only salivary gland function reduction by aging but also multiple chronic diseases and therapeutic agents for such diseases reduce the amount of saliva secretion; therefore, many people currently complain of dry mouth.

The reduction of salivary secretion makes the mouth dry, which leads to difficulty in chewing and swallowing, and lowers digestive function. Dry mouth also causes an unpleasant sensation in the mouth, and halitosis. Further progression of such symptoms causes periodontal diseases and infectious diseases in the mouth, such as stomatitis. Therefore, there is a need to increase the amount of salivary secretion by some kind of means.

As means for increasing the amount of saliva secretion, a gustatory stimulation method using acidulation (Patent Literature (PTL) 1) and an olfactory stimulation method (PTL 2) have been proposed. Methods using a plant extract having a salivation-promoting effect or a component of the plant extract (PTL 3 to PTL 8), a method using a pharmaceutical substance targeting a muscarinic receptor (PTL 9), and a method using a pharmaceutical substance targeting PAR-2 (PTL 10) have also been proposed.

However, some of the methods disclosed in the above documents are insufficient in terms of strength and sustainability of the effect, and also have the following problems. The method disclosed in PTL 1 finds only limited use in view of palatability. Furthermore, because of strong stimulation, frequent use of this method may affect oral tissues, such as dissolution of the teeth, stimulation of oral mucosa, etc. The method disclosed in PTL 2 has a problem such that the effect is lost with the disappearance of olfactory stimuli. The methods disclosed in PTL 3 to PTL 6 have a problem such that the methods can be applied to only limited types of compositions (food compositions, and compositions for intraoral use) because many of the plant extracts used in these methods have a specific stimulus, taste, and flavor, and using such extracts with an organic acid is essential or recommended. Further, the methods disclosed in PTL 9 and PTL 10 use pharmaceutical substances; therefore, the use of such methods may be limited.

Quercetin, a kind of flavonoid, has recently been reported to have a salivation-enhancing effect (Non-patent Literature (NPL) 1). More specifically, it has been reported that administering quercetin to model mice having disturbance of salivary secretion created by radiation exposure reduces hyposalivation, and that administering quercetin to normal mice enhances saliva secretion. With respect to the action mechanism of quercetin in the saliva secretion, NPL 1 discloses that saliva secretion is promoted by enhancing the expression of aquaporin 5 and uptake of ions into cells. However, these are all data of quercetin intake by mice. NPL1 nowhere mentions a case of quercetin intake by humans.

CITATION LIST

Patent Literature

PTL 1: JPH7-101856A
PTL 2: JP2003-40752A
PTL 3: JPH11-71253A
PTL 4: JPH10-182392A
PTL 5: JP2002-265375A
PTL 6: JP2005-162633A
PTL 7: WO2009/060915
PTL 8: JP2009-531287A
PTL 9: JPH8-12575A
PTL 10: JP2001-64203A

Non-Patent Literature (NPL)

Non-patent Literature (NPL) 1: Ichiro Saito et al., PLOS ONE, DOI, 10.1371/journal.pone.0116008 Jan. 28, 2015

SUMMARY OF INVENTION

Technical Problem

An object of the present invention is to provide a salivator, preferably a salivator that is used in the mouth of a human, or used by oral administration to a human; and that promptly promotes saliva secretion after intraoral application or oral administration (intake) of the salivator, and can heal the dry mouth.

Further, another object of the present invention is to provide an additive that is effective in preparing a composition for intraoral use or oral intake (a food or beverage, a pharmaceutical product) that is capable of promoting saliva secretion (an additive for a composition for intraoral use or oral intake); and preferably an additive effective in preparing a composition for intraoral use or oral intake that is capable of promoting saliva secretion in a person with reduced salivation function, and assisting chewing and swallowing. The additive is preferably an additive suitable for compositions for intraoral use or oral intake that can impart the above effects to compositions for intraoral use or oral intake without giving undesirable simulation or flavor (taste, smell) to the mouth, or providing side effects that are harmful to human bodies. Another object of the present invention is to provide a method for preparing the composition for intraoral use or oral intake by using the additive. A further object of the present invention is to provide the composition for intraoral use or oral intake comprising the additive.

Solution to Problem

The present inventors conducted extensive research to achieve the above objects, and found that enzymatically modified isoquercitrin has a salivation-promoting effect. More specifically, as shown in Experimental Example 1 described below, the present inventors found that application of enzymatically modified isoquercitrin to the mouth of a human, or oral intake of enzymatically modified isoquercitrin promptly promotes saliva secretion and increases the amount of secretion. In contrast, when α-glucosylrutin, which, like enzymatically modified isoquercitrin, is a quercetin glycoside having a quercetin structure, or quercetin itself was administered to a human in an equimolar amount relative to the enzymatically modified isoquercitrin, in terms of rutin, no salivation-promoting effect (saliva secretion-increasing effect) was confirmed. These results confirm that, among the above-mentioned flavonoids, only enzymatically modified isoquercitrin can immediately exhibit a salivation-promoting effect (saliva secretion-increasing effect) by application to the mouth of a human or oral administration to a human, and that this effect is specific to enzymatically modified isoquercitrin. Further, as shown in Experimental Example 2, the salivation-promoting effect (saliva secretion-increasing effect) of the enzymatically modified isoquercitrin is significantly increased by using a polysaccharide for thickening with the enzymatically modified isoquercitrin, or by thickening the test sample. Such enhancement of the salivation-promoting effect (saliva secretion-increasing effect) by incorporating a thickening polysaccharide or by thickening is also specific to enzymatically modified isoquercitrin, and was not observed in α-glucosylrutin or quercetin itself.

The present inventors conducted further research based on this finding, and confirmed that, in particular, when a thickening polysaccharide is used in a proportion of 0.2 to 500 parts by mass per part by mass of enzymatically modified isoquercitrin, the salivation-promoting effect of the enzymatically modified isoquercitrin can be enhanced without significantly affecting palatability (taste, smell, etc.) of the target composition for intraoral use or oral intake (a food or beverage, a composition).

The present inventors conducted further research based on these findings, and have accomplished the present invention. The present invention includes the following embodiments.

(A) Use as Salivator (A-I) Salivator (A-I-1) A salivator comprising enzymatically modified isoquercitrin as an active ingredient.
(A-I-2) The salivator according to (I-1), further comprising a thickening polysaccharide.
(A-I-3) The salivator according to (A-I-1) or (A-I-2), wherein the thickening polysaccharide is at least one member selected from the group consisting of xanthan gum, locust bean gum, guar gum, tara gum, deacylated gellan gum, highly acylated gellan gum, pectin, alginates, gelatin, agar, *psyllium* seed gum, and carrageenan.
(A-I-4) The salivator according to any one of (A-I-1) to (A-I-3), which is a composition for intraoral use or oral intake.
(A-I-5) The salivator according to any one of (A-I-1) to (A-I-4), which is a composition for intraoral use or oral intake, the composition being for a human with reduced salivation function (a person with reduced salivation function), or a human with reduced swallowing function (a person with reduced deglutition function).
(A-I-6) The salivator according to any one of (A-I-1) to (A-I-5), which is a composition for intraoral use or oral intake, the composition being for a healthy person whose mouth is in a dry state. The mouth in a dry state is not particularly limited. Examples include the mouth in a dry state on exercising, bathing, waking, etc.
(A-I-7) The salivator according to any one of (A-I-1) to (A-I-6), wherein the salivator is in the form of a syrup, health drink, liquid, emulsion, oil, spray, gel, paste, tablet, chewable agent, lozenge, pill, granule, powder (powdered medicine), dry syrup, film, or stick-shaped preparation.

The "salivator" of the present invention promotes salivation to thereby achieve the effect of increasing the amount of saliva secretion. In this meaning, the embodiment of the present invention includes "saliva secretion (amount) increasing agents."

(A-II) Method for Preparing Salivator (A-II-1) A method for preparing a salivator, comprising incorporating enzymatically modified isoquercitrin.
(A-II-2) The method according to (A-II-I), comprising further incorporating a thickening polysaccharide.
(A-II-3) The method according to (A-II-I) or (A-II-2), wherein the thickening polysaccharide is at least one member selected from the group consisting of xanthan gum, locust bean gum, guar gum, tara gum, deacylated gellan gum, highly acylated gellan gum, pectin, alginates, gelatin, agar, *psyllium* seed gum, and carrageenan.
(A-II-4) The method according to any one of (A-II-I) to (A-II-3), further comprising processing the salivator into a form for intraoral use or oral administration.
(A-II-5) The method according to any one of (A-II-I) to (A-II-4), wherein the form for intraoral use or oral administration is a syrup, health drink, liquid, emulsion, oil, spray, gel, paste, tablet, chewable agent, lozenge, pill, granule, powder (powdered medicine), dry syrup, film, or stick-shaped preparation.

(A-III) Use for producing salivator (A-III-1) Use of enzymatically modified isoquercitrin for producing a salivator.
(A-III-2) Use of enzymatically modified isoquercitrin and a thickening polysaccharide for producing a salivator.
(A-III-3) The use according to (A-III-2), wherein in the production of a salivator, the enzymatically modified isoquercitrin and the thickening polysaccharide are used separately, or in the form of a composition.
(A-III-4) The use according to (A-III-2) or (A-III-3), wherein the thickening polysaccharide is at least one member selected from the group consisting of xanthan gum, locust bean gum, guar gum, tara gum, deacylated gellan gum, highly acylated gellan gum, pectin, alginates, gelatin, agar, *psyllium* seed gum, and carrageenan.
(A-III-5) The use according to any one of (A-III-1) to (A-III-4), wherein the salivator is in a form for intraoral use or oral administration.
(A-III-6) The use according to any one of (A-III-1) to (A-III-5), wherein the form for intraoral use or oral administration is a form of a syrup, health drink, liquid, emulsion, oil, spray, gel, paste, tablet, chewable agent, lozenge, pill, granule, powdered medicine (powder), dry syrup, film, or stick-shaped preparation.

(A-IV) Method for Promoting Salivation (A-IV-I) A method for promoting saliva secretion in a subject, comprising allowing the subject to orally ingest an effective amount of the salivator according to any one of (A-I-I) to (A-I-6).
(A-IV-2) the Method According to (A-IV-1), Wherein the Subject is a human with reduced saliva secretion function (a person with reduced saliva secretion function) or a human with reduced swallowing function (a person with reduced deglutition function).
(A-IV-3) The method according to (A-IV-1) or (A-IV-2), wherein the subject is a human with hyposalivation or xerostomia.
(A-IV-4) The method according to any one of (A-IV-1) to (A-IV-3), wherein the subject is a healthy person whose mouth is in a dry state. The mouth in a dry state is not particularly limited. Examples include the mouth in a dry state on exercising, bathing, waking, etc.

The "method for promoting salivation" of the present invention also achieves the effect of increasing the amount of salivation by conducting the method. In that meaning, this invention also includes "a method for increasing saliva secretion (amount)."

(B) Use as an Additive for a Composition for Intraoral Use or Oral Intake

(I) Additive for a Composition for Intraoral Use or Oral Intake (B-I-1) An additive for a composition for intraoral use or oral intake comprising enzymatically modified isoquercitrin and a thickening polysaccharide.
(B-I-2) The additive for a composition for intraoral use or oral intake according to (B-I-1), wherein the thickening polysaccharide is at least one member selected from the group consisting of xanthan gum, locust bean gum, guar gum, tara gum, deacylated gellan gum, highly acylated gellan gum, pectin, alginates, gelatin, agar, *psyllium* seed gum, and carrageenan.
(B-I-3) The additive for a composition for intraoral use or oral intake according to (B-I-1) or (B-I-2), which contains the thickening polysaccharide in a proportion of 0.2 to 500 parts by mass per part by mass of the enzymatically modified isoquercitrin.
(B-I-4) The additive for a composition for intraoral use or oral intake according to (B-I-1) or (B-I-2), which is an additive for preparing a sol composition for intraoral use or oral intake and contains the thickening polysaccharide in a proportion of 0.2 to 400 parts by mass, preferably 0.3 to 350 mass by parts, and more preferably 0.4 to 300 parts by mass, per part by mass of the enzymatically modified isoquercitrin.
(B-I-5) The additive for a composition for intraoral use or oral intake according to (B-I-1) or (B-I-2), which is an additive for preparing a gel composition for intraoral use or oral intake, and contains the thickening polysaccharide in a proportion of 1 to 500 parts by mass, preferably 2 to 450 parts by mass, and more preferably 2.5 to 350 parts by mass, per part by mass of the enzymatically modified isoquercitrin.
(B-I-6) The additive for a composition for intraoral use or oral intake according to (B-I-1) or (B-I-2), which is an additive for preparing a processed grain food or beverage, and contains the enzymatically modified isoquercitrin in a proportion of 0.01 to 3000 parts by mass, preferably 0.05 to 2000 parts by mass more, and more preferably 0.1 to 1200 parts by mass, per part by mass of the enzymatically modified isoquercitrin.
(B-I-7) The additive for a composition for intraoral use or oral intake according to any one of (B-I-1) to (B-I-6), which is an additive in at least one form selected from the group consisting of solids, pastes, and liquids.
(B-I-8) The additive for a composition for intraoral use or oral intake according to any one of (B-I-1) to (B-I-7), wherein the composition for intraoral use or oral intake is a food or beverage or a pharmaceutical product.
(B-I-9) The additive for a composition for intraoral use or oral intake according to any one of (B-I-1) to (B-I-8), wherein the composition for intraoral use or oral intake is a food or beverage or a pharmaceutical product that is ingested by or administered to at least one person selected from the group consisting of persons with reduced salivation function, persons with reduced swallowing function, and persons with reduced chewing function.
(B-I-10) The additive for a composition for intraoral use or oral intake according to any one of (B-I-1) to (B-I-9), which is an additive for preparing a composition for intraoral use or oral intake in the form of a gel having at least one of the following physical properties (1) and (2), or in the form of a sol having the following physical property (3):
(1) fracture strain: 0.3 to 0.8;
(2) hardness: 500 to 500,000 N/m$^2$; and
(3) viscosity: 0.006 to 0.6 Pa·s.
(B-I-11) The additive for a composition for intraoral use or oral intake according to any one of (B-I-1) to (B-I-10), which is used for one of the following (a) to (c):
 (a) a salivator that imparts a salivation-promoting effect to a composition for intraoral use or oral intake:
 the salivator can be preferably used for preparing a composition for intraoral use or oral intake (a food or beverage, a pharmaceutical product), the composition being for a person having reduced salivation function (a person with reduced salivation function);
 (b) a swallowing-assisting agent that imparts an easy-to-swallow property to the composition for oral intake:
 the swallowing-assisting agent can be preferably used for preparing a composition for oral intake (a food or beverage, a pharmaceutical product), the composition being for a person having reduced swallowing function (a person with reduced deglutition function); and (c) a chewing-assisting agent that imparts an easy-to-chew property to a composition for oral intake:

the chewing-assisting agent can be preferably used to prepare a composition for oral intake (a food or beverage, a pharmaceutical product), the composition being for a person having reduced chewing function (a person with reduced mastication function).

(B-II) Composition for Intraoral Use or Oral Intake, and Method for Preparation Thereof (B-II-1) A composition for intraoral use or oral intake comprising the additive for a composition for intraoral use or oral intake according to any one of (B-I-1) to (B-I-11).
(B-II-2) The composition for intraoral use or oral intake according to (B-II-1), which is a food or beverage, or a pharmaceutical product.
(B-II-3) The composition for intraoral use or oral intake according to (B-II-1) or (B-II-2), which is a food or beverage or a pharmaceutical product ingested by or administered to at least one person selected from the group consisting of persons with reduced salivation function, persons with reduced swallowing function, and persons with reduced chewing function.
(B-II-4) The composition for intraoral use or oral intake according to any one of (B-II-1) to (B-II-3), which is a food or beverage for healthy persons whose mouth is in a dry state.

The mouth in a dry state is not particularly limited. Examples include the mouth in a dry state on exercising, bathing, waking, etc.
(B-II-5) The composition for intraoral use or oral intake according to any one of (B-II-1) to (B-II-4), which is a food or beverage or a pharmaceutical product for intraoral use or oral intake that is in the form of a gel having at least one of the following physical properties (1) and (2), or in the form of a sol having the following physical property (3):
(1) fracture strain: 0.3 to 0.8
(2) hardness: 500 to 500,000 N/m$^2$
(3) viscosity: 0.006 to 0.6 Pa·s.
(B-II-6) A method for preparing the composition for intraoral use or oral intake according to any one of (B-II-1) to (B-II-5), comprising incorporating enzymatically modified isoquercitrin and a thickening polysaccharide, or the additive for a composition for intraoral use or oral intake according to any one of (B-I-1) to (B-I-11) into a food or beverage or a pharmaceutical product for intraoral use or oral administration each having a water content of 60 mass % or more.

(B-III) Various Applications of Enzymatically Modified Isoquercitrin (B-III-1-1) A method for enhancing the salivation-promoting effect of enzymatically modified isoquercitrin, the method being characterized by using a thickening polysaccharide with the enzymatically modified isoquercitrin.
(B-III-1-2) The enhancement method according to (B-III-1-1), wherein the thickening polysaccharide is at least one member selected from the group consisting of xanthan gum, locust bean gum, guar gum, tara gum, deacylated gellan gum, highly acylated gellan gum, pectin, alginates, gelatin, agar, *psyllium* seed gum, and carrageenan.
(B-III-1-3) The enhancement method according to (B-III-1-1) or
(B-III-1-2), wherein the thickening polysaccharide is used in a proportion of 0.2 to 500 parts by mass per part by mass of the enzymatically modified isoquercitrin.
(B-III-1-4) The enhancement method according to any one of (B-III-1-1) to (B-III-1-3), comprising forming a gel having at least one of the following physical properties (1) and (2), or a sol having the following physical property (3) by using the thickening polysaccharide with the enzymatically modified isoquercitrin:
(1) fracture strain: 0.3 to 0.8;
(2) hardness: 500 to 500,000 N/m$^2$; and
(3) viscosity: 0.006 to 0.6 Pa·s.
(B-III-1-5) The enhancement method according to (B-III-1-4) comprising forming a sol by using the thickening polysaccharide in a proportion of 0.2 to 400 parts by mass, preferably 0.3 to 350 parts by mass, and more preferably 0.4 to 300 parts by mass, per part by mass of the enzymatically modified isoquercitrin.
(B-III-1-6) The enhancement method according to (B-III-1-4), comprising forming a gel by using the thickening polysaccharide in a proportion of 1 to 500 parts by mass, preferably 2 to 450 parts by mass, and more preferably 2.5 to 350 parts by mass, per part by mass of the enzymatically modified isoquercitrin.
(B-III-1-7) The enhancement method according to any one of (B-III-1-1) to (B-III-1-4), comprising preparing a processed grain food or beverage, wherein the processed grain food or beverage contains the thickening polysaccharide in a proportion of 0.01 to 3000 parts by mass, preferably 0.05 to 2000 parts by mass, and more preferably 0.1 to 1200 parts by mass, per part by mass of the enzymatically modified isoquercitrin.
(B-III-2-1) A method for promoting salivation in a person with reduced salivation function, comprising allowing a composition for intraoral use or oral intake comprising enzymatically modified isoquercitrin and a thickening polysaccharide to be orally administered to or ingested by the person with reduced salivation function.
(B-III-2-2) The salivation-promoting method according to (B-III-2-1), wherein the thickening polysaccharide is at least one member selected from the group consisting of xanthan gum, locust bean gum, guar gum, tara gum, deacylated gellan gum, highly acylated gellan gum, pectin, alginates, gelatin, agar, *psyllium* seed gum, and carrageenan.
(B-III-2-3) The salivation-promoting method according to (B-III-2-1) or (B-III-2-2), wherein the composition for intraoral use or oral intake comprises the thickening polysaccharide in a proportion of 0.2 to 500 parts by mass per part by mass of the enzymatically modified isoquercitrin.
(B-III-2-4) The salivation-promoting method according to (B-III-2-1) or (B-III-2-2), wherein the composition for intraoral use or oral intake is in the form of a sol, and comprises the thickening polysaccharide in a proportion of 0.2 to 400 parts by mass, preferably 0.3 to 350 parts by mass, and more preferably 0.4 to 300 parts by mass, per part by mass of the enzymatically modified isoquercitrin.
(B-III-2-5) The salivation-promoting method according to (B-III-2-4), wherein the composition for intraoral use or oral intake is in the form of a gel, and contains the thickening polysaccharide in a proportion of 1 to 500 parts by mass, preferably 2 to 450 parts by mass, and more preferably 2.5 to 350 parts by mass, per part by mass of the enzymatically modified isoquercitrin.
(B-III-2-6) The salivation-promoting method according to (B-III-2-4), wherein the composition for intraoral use or oral intake is a processed grain food or beverage, and contains the thickening polysaccharide in a proportion of 0.01 to 3000 parts by mass, preferably 0.05 to 2000 parts by mass, and more preferably 0.1 to 1200 parts by mass, per part by mass of the enzymatically modified isoquercitrin.

(B-III-2-7) The salivation-promoting method according to any one of (B-III-2-1) to (B-III-2-6), wherein the composition for intraoral use or oral intake is a food or beverage or a pharmaceutical product.

(B-III-2-8) The salivation-promoting method according to any one of (B-III-2-1) to (B-III-2-7), wherein the composition for intraoral use or oral intake is a food or beverage, or a pharmaceutical product in the form of a gel having at least one of the following physical properties (1) and (2), or in the form of a sol having the following physical property (3):

(1) fracture strain: 0.3 to 0.8;

(2) hardness: 500 to 500,000 N/m$^2$; and (3) viscosity: 0.006 to 0.6 Pa·s.

(B-III-3-1) A composition for intraoral use or oral intake comprising enzymatically modified isoquercitrin and a thickening polysaccharide, the composition being used for a person with reduced salivation function to ameliorate reduction in saliva secretion or promote saliva secretion.

(B-III-3-2) The composition for intraoral use or oral intake according to (B-III-3-1), wherein the thickening polysaccharide is at least one member selected from the group consisting of xanthan gum, locust bean gum, guar gum, tara gum, deacylated gellan gum, highly acylated gellan gum, pectin, alginates, gelatin, agar, *psyllium* seed gum, and carrageenan.

(B-III-3-3) The composition for intraoral use or oral intake according to (B-III-3-1) or (B-III-3-2), wherein the composition for intraoral use or oral intake contains the thickening polysaccharide in a proportion of 0.2 to 500 parts by mass per part by mass of the enzymatically modified isoquercitrin.

(B-III-3-4) The composition for intraoral use or oral intake according to (B-III-3-1) or (B-III-3-2), which is in the form of a sol and contains the thickening polysaccharide in a proportion of 0.2 to 400 parts by mass, preferably 0.3 to 350 parts by mass, and more preferably 0.4 to 300 parts by mass, per part by mass of the enzymatically modified isoquercitrin.

(B-III-3-5) The composition for intraoral use or oral intake according to (B-III-3-1) or (B-III-3-2), which is in the form of a gel and contains the thickening polysaccharide in a proportion of 1 to 500 parts by mass, preferably 2 to 450 parts by mass, and more preferably 2.5 to 350 parts by mass, per part by mass of the enzymatically modified isoquercitrin.

(B-III-3-6) The composition for intraoral use or oral intake according to any one of (B-III-3-1) to (B-III-3-5), wherein the composition for intraoral use or oral intake is a processed grain food or beverage, and contains the thickening polysaccharide in a proportion of 0.01 to 3000 parts by mass, preferably 0.05 to 2000 parts by mass, and more preferably 0.1 to 1200 parts by mass, per part by mass of the enzymatically modified isoquercitrin.

(B-III-3-7) The composition for intraoral use or oral intake according to any one of (B-III-3-1) to (B-III-3-6), which is a food or beverage or a pharmaceutical product for intraoral use or oral intake.

(B-III-3-8) The composition for intraoral use or oral intake according to any one of (B-III-3-1) to (B-III-3-7), which is a food or beverage or a pharmaceutical product in the form of a gel having at least one of the following physical properties (1) and (2), or in the form of a sol having the following physical property (3):

(1) fracture strain: 0.3 to 0.8;

(2) hardness: 500 to 500,000 N/m$^2$; and (3) viscosity: 0.006 to 0.6 Pa·s.

Advantageous Effects of Invention

Intake or administration of the salivator of the present invention to a human can promote saliva secretion in the human. Intake or administration of the salivator to a human with reduced salivation function can ameliorate the reduction of saliva secretion in the human. Further, promoting salivation by using the salivator of the present invention can enhance a self-cleaning effect in the mouth, and can also prevent various negative effects caused by reduction in saliva secretion (such as dry mouth, unpleasant sensation in the mouth, taste disorder, halitosis, dental caries, periodontal diseases, infection of mucosa, and like mouth dysfunctions; difficulty in conversation and utterance; etc.). Further, the salivator of the present invention, which promotes salivation, can facilitate swallowing by humans with difficulty in swallowing due to reduced saliva secretion.

Further, since the salivator of the present invention uses as an active ingredient enzymatically modified isoquercitrin, which has a history of usage as a food, the salivator is highly safe, and can be preferably used as a composition for intraoral use or oral intake that is continuously used in the mouth or orally administered (e.g., pharmaceutical products, quasi-drugs, foods and beverages (including functional foods and beverages, and health foods and beverages)). The salivator of the present invention can be used as a pharmaceutical product for intraoral use or oral administration, and can be preferably used as a functional food or beverage or a health food or beverage in alternative medicine, or complementary and alternative medicine.

The additive for a composition for intraoral use or oral intake of the present invention can impart a salivation-promoting effect, easy-to-swallow property, and/or easy-to-chew property to a composition for intraoral use or oral intake, such as a food or beverage or a pharmaceutical product. Therefore, the additive can be preferably used to prepare a food or beverage or a pharmaceutical product for intraoral use or oral administration, which is ingested by or administered to a person with reduced salivation function, a person with reduced swallowing function, or a person with reduced chewing function. In particular, since the additive for a composition for intraoral use or oral intake of the present invention that contains a thickening polysaccharide in a proportion of 0.2 to 500 parts by mass per part by mass of the enzymatically modified isoquercitrin hardly affects palatability (taste, smell, etc.), this additive can be used for preparing a composition for intraoral use or oral intake without severe restrictions on the amount to be added.

Further, the composition for intraoral use or oral intake of the present invention, which contains the additive for a composition for intraoral use or oral intake, has a salivation-promoting effect, easy-to-swallow property and/or easy-to-chew property; and can be preferably used as a food or beverage or a pharmaceutical product for intraoral use or oral administration that is ingested by or administered to a person with reduced salivation function, a person with reduced swallowing function, or a person with reduced chewing function.

According to the method of the present invention, the use of a thickening polysaccharide with enzymatically modified isoquercitrin can enhance the salivation-promoting effect of the enzymatically modified isoquercitrin. Accordingly, when an oral composition containing a thickening polysaccharide in addition to enzymatically modified isoquercitrin is ingested by or administered to a subject with reduced salivation function, saliva secretion is promoted in the subject, thereby ameliorating reduction in saliva secretion.

DESCRIPTION OF EMBODIMENTS

(A-I) Salivator (A-I-1) Enzymatically Modified Isoquercitrin

Figure 1:
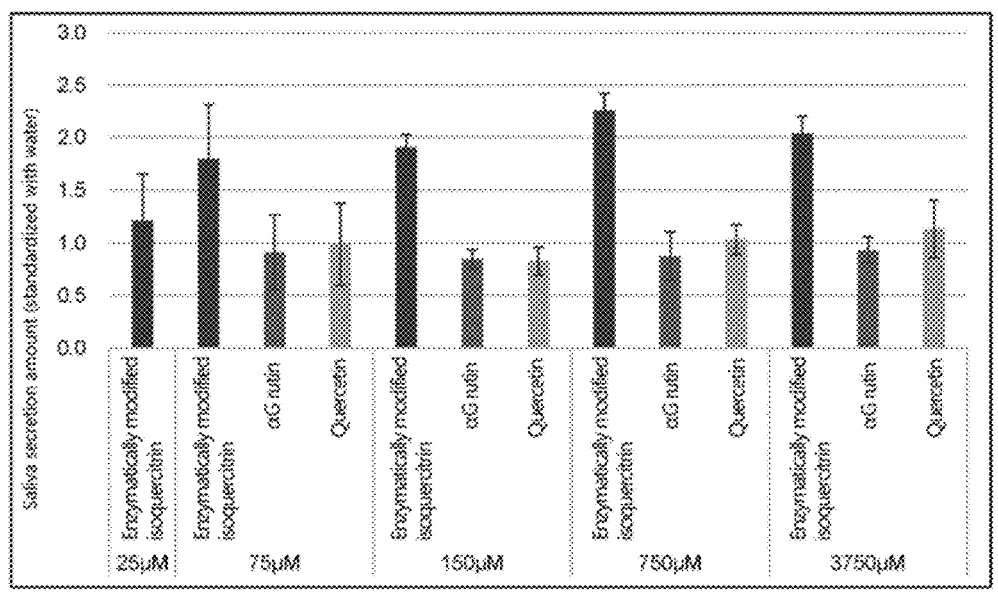
FIG. 1 is a graph showing the measurement results of salivation-promoting effects in Experimental Example 1. The amount of saliva secreted is shown as a relative value, with the amount of saliva secreted by ingestion of water being set as 1 (the same applies in FIG. 2).

The salivator of the present invention is characterized in that the promoter contains enzymatically modified isoquercitrin (English name: enzymatically modified isoquercitrin) as an active ingredient. The enzymatically modified isoquercitrin contains a-glucosyl isoquercitrin represented by the following formula as a main component, and is also called sugar-transferred isoquercitrin.

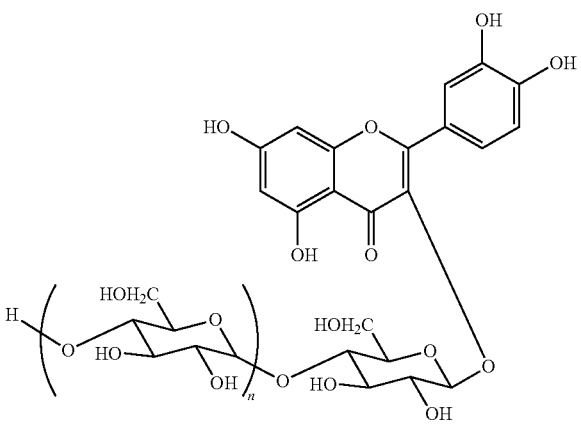

In the above formula, n represents an integer of 0 to 10.

α-Glucosyl isoquercitrin contained in the enzymatically modified isoquercitrin may be one compound wherein n is an integer of 0 to 10, or a mixture of two or more compounds wherein n is an integer of 0 to 10. Preferably, the α-glucosyl isoquercitrin is a mixture, and more preferably is a mixture of two or more compounds wherein n is an integer of 0 to 6. α-Glucosyl isoquercitrin wherein n is 0 is also referred to as isoquercitrin. In the present invention, an enzymatically modified isoquercitrin containing α-glucosyl isoquercitrin in an amount of 60 mass % or more in terms of rutin is preferably used.

The α-glucosyl isoquercitrin content of enzymatically modified isoquercitrin is shown in terms of rutin because rutin and α-glucosyl isoquercitrin have the same molar extinction coefficient at a wavelength of 351 nm, and rutin is more readily available than α-glucosyl isoquercitrin. Therefore, in this technical field, it is common practice to quantify the α-glucosyl isoquercitrin content of enzymatically modified isoquercitrin in terms of rutin by UV-visible absorbance spectroscopy using rutin as a standard sample.

Specifically, the α-glucosyl isoquercitrin content of enzymatically modified isoquercitrin can be calculated in terms of rutin by the following quantification method described in the "Enzymatically Modified Isoquercitrin" column in The Japanese Standards of Food Additives, 8th edition (The Ministry of Health, Labour and Welfare).

Quantification (i) The target enzymatically modified isoquercitrin (target sample) is dried, and about 0.05 g of enzymatically modified isoquercitrin is accurately weighed and dissolved in water to make the total volume exactly 100 ml. Filtration may be performed, if necessary. 4 ml of this solution is accurately measured, and a phosphoric acid solution (an aqueous solution prepared by dissolving 1 g of phosphoric acid in water to make a total volume of 1000 ml; the same applies hereinafter) is added to make the total volume 100 ml, thus preparing a test liquid.

(ii) Separately, rutin for quantification is dried at 135° C. for 2 hours. About 0.05 g of the rutin is accurately weighed and dissolved in methanol to make the total volume exactly 100 ml. 4 ml of this solution is accurately measured, and the phosphoric acid solution is added to make the total volume exactly 100 ml, thus preparing a standard liquid.

(iii) The absorbance of the test liquid (At) and standard liquid (As) at a wavelength of 351 nm is measured by UV-visible absorbance spectroscopy using the phosphoric acid solution as a control. The α-glucosyl isoquercitrin content in terms of rutin is calculated by the following formula.

α-Glycosyl isoquercitrin content (as rutin $(C_{27}H_{30}O_{16})$)=(Amount of rutin for quantification sampled (g)/Amount of Test Sample sampled (g)×(At/As)×100(mass %)) [Math. 1]

Enzymatically modified isoquercitrin can be generally prepared by adding glucose to a mixture of isoquercitrin and starch or dextrin by using cyclodextrin glucosyltransferase. Isoquercitrin is generally obtained by enzymatic degradation of rutin. Isoquercitrin can also be obtained by other known methods (such as degradation of rutin, extractive isolation from a plant, and glycosidation of quercetin). Conveniently, the pharmaceutical preparation containing enzymatically modified isoquercitrin is commercially available. Examples of such commercially available products include "San Emiq No. 1" produced by San-Ei Gen F.F.I., Inc. "San Emiq" is a registered trademark of San-Ei Gen F.F.I., Inc. The enzymatically modified isoquercitrin contained in "San Emiq No. 1" is a mixture of two or more compounds represented by the above formula wherein n is selected from 0 to 6. San Emiq No. 1 contains α-glucosyl isoquercitrin as a main component in an amount of 60 mass % or more in terms of rutin. "San Emiq No. 1" contains α-glucosyl isoquercitrin in an amount of 10 mass % in terms of rutin by the above quantification method, and further contains dextrin as another component.

The salivator of the present invention may be any promoter containing enzymatically modified isoquercitrin, as long as it provides a salivation-promoting effect. The enzymatically modified isoquercitrin content is not particularly limited, and can be appropriately selected from the range of 0.001 to 0.5 mass % as α-glucosyl isoquercitrin (in terms of rutin $[C_{27}H_{30}O_{16}]$). In this specification, the enzymatically modified isoquercitrin content is shown as the α-glucosyl isoquercitrin content (in terms of rutin $[C_{27}H_{30}O_{16}]$) (mass %), unless otherwise specified. Accordingly, in the present invention (this specification), "1 part by mass of enzymatically modified isoquercitrin" means that the amount of α-glucosyl isoquercitrin contained in enzymatically modified isoquercitrin is 1 part by mass in terms of rutin $[C_{27}H_{30}O_{16}]$.

(A-I-2) Polysaccharides for Thikening

The salivator of the present invention may contain a thickening polysaccharide in addition to enzymatically modified isoquercitrin.

As shown in the Experimental Examples below, a salivator containing a thickening polysaccharide in addition to enzymatically modified isoquercitrin can provide a higher salivation-promoting effect than the corresponding salivator not containing a thickening polysaccharide.

The thickening polysaccharide to be used in the present invention is an edible thickening polysaccharide that is allowed to be used in a food or beverage or a pharmaceutical product for oral administration. Examples of thickening polysaccharides include xanthan gum, galactomannan (e.g., locust bean gum, guar gum, tara gum, etc.), deacylated gellan gum, highly acylated gellan gum, carrageenan (e.g., kappa-carrageenan, iota-carrageenan, lambda-carrageenan, etc.), tamarind seed gum, glucomannan, psyllium seed gum, macrophomopsis gum, agar, gelatin, pectin (e.g., HM pectin, LM pectin, etc.), alginic acid, alginates (alginic acid salts) (e.g., sodium alginate, potassium alginate, calcium alginate, etc.), pullulan, curdlan, gum tragacanth, ghatti gum, gum arabic, arabinogalactan, karaya gum, furcellaran, chitin, welan gum, celluloses (e.g., sodium carboxymethyl cellulose, carboxymethyl cellulose calcium, carboxymethyl cellulose, hydroxypropyl cellulose, hydroxypropyl methylcellulose, hydroxypropyl ethylcellulose, hydroxyethylcellulose, hydroxymethylcellulose, ethyl cellulose, methyl cellulose, fermented cellulose, crystalline cellulose, etc.), starches (e.g., starch, sodium carboxymethyl starch, carboxymethyl starch, hydroxypropyl starch, gelatinized starch, phosphoric acid-crosslinked starch, octenylsuccinic acid starch, starch acetate, etc.), dextrins (e.g., polydextrose, indigestible dextrin, etc.), soybean polysaccharides, and the like.

In the present invention, among the thickening polysaccharides, at least one member selected from the group consisting of xanthan gum, locust bean gum, guar gum, tara gum, deacylated gellan gum, highly acylated gellan gum, pectin, alginates, gelatin, agar, psyllium seed gum, and carrageenan is preferable. More preferably, the thickening polysaccharide is at least one member selected from the group consisting of xanthan gum, locust bean gum, guar gum, deacylated gellan gum, highly acylated gellan gum, pectin, and carrageenan. Particularly preferably, the thickening polysaccharide is at least one member selected from the group consisting of xanthan gum, pectin, and carrageenan. These thickening polysaccharides can be used singly, or in a combination of two or more. The combination of two or more thickening polysaccharides is not particularly limited. Examples include a combination of xanthan gum and guar gum; a combination of xanthan gum and locust bean gum; a combination of xanthan gum and carrageenan; a combination of xanthan gum, guar gum, and locust bean gum; and a combination of deacylated gellan gum and highly acylated gellan gum. Further, at least one member selected from the group consisting of these thickening polysaccharides can be used in combination with at least one member selected from the group consisting of the thickening polysaccharides described above.

The proportion of the thickening polysaccharide to the enzymatically modified isoquercitrin in the salivator of the present invention can be usually selected from the range of 0.2 to 500 parts by mass per part by mass of the enzymatically modified isoquercitrin (in terms of rutin; the same applies hereinafter). For example, when the salivator of the present invention is in the form of a solid, such as a tablet, granule or powder (powdered medicine), or dry syrup, the proportion of the thickening polysaccharide may be, for example, 0.2 to 500 parts by mass, preferably 0.3 to 400 parts by mass, and more preferably 0.4 to 350 parts by mass, per part by mass of the enzymatically modified isoquercitrin. When the salivator of the present invention is in the form of a paste, the proportion of the thickening polysaccharide may be, for example, 0.2 to 500 parts by mass, preferably 0.3 to 400 parts by mass, and more preferably 0.4 to 350 parts by mass, per part by mass of the enzymatically modified isoquercitrin. When the salivator of the present invention is in the form of a liquid, the proportion of the thickening polysaccharide may be, for example, 0.2 to 400 parts by mass, preferably 0.3 to 350 parts by mass, and more preferably 0.3 to 300 parts by mass, per part by mass of the enzymatically modified isoquercitrin. When the salivator of the present invention is in the form of a gel (jelly), the proportion of the thickening polysaccharide may be, for example, 1 to 500 parts by mass, and preferably 2 to 450 parts by mass, and more preferably 2.5 to 350 parts by mass, per part by mass of the enzymatically modified isoquercitrin.

As described above, the proportion of the thickening polysaccharide contained in the salivator of the present invention varies according to the form of the salivator. For example, when the form of the salivator is a solid form such as a tablet, chewable agent, lozenge, granule, powder (powdered medicine), dry syrup, film, or stick-like preparation, the proportion of the thickening polysaccharide can be appropriately selected from the range of 1 mass % or more to 99.9 mass % or less. The proportion of the thickening polysaccharide is preferably 3 to 90 mass %, and more preferably 5 to 80 mass % more. When the form of the salivator is a paste or liquid form (including a syrup, health drink, liquid, emulsion, oil, and spray), the proportion of the thickening polysaccharide can be appropriately selected from the range of 0.02 to 30 mass %, preferably 0.02 to 10 mass %, and more preferably 0.02 to 8 mass %. When the salivator is in the form of a gel, the proportion of the thickening polysaccharide per part by mass of the enzymatically modified isoquercitrin may be appropriately selected from the range of 0.02 to 10 mass %. Preferably, the proportion of the thickening polysaccharide is 0.02 to 8 mass %, and more preferably 0.02 to 6 mass %.

(A-I-3) Other Components

The salivator of the present invention may contain any edible components in addition to the above components, as long as the effect of the present invention is not impaired.

Examples of edible components include edible metal salts, excipients, organic acids, coloring agents, amino acids (e.g., glycine, arginine, lysine, alanine, glutamic acid, histidine, threonine, asparagine, aspartic acid, phenylalanine, leucine, valine, serine, tyrosine, isoleucine, methionine, etc.), nutrients (including vitamins and minerals), antioxidants, preservatives, antimicrobial agents, bacteriostatic agents, plant extracts (e.g., tea extracts, coffee extracts, cocoa extracts, etc.), fruit juices (e.g., orange, grape, apple, peach, pineapple, tomato, strawberry, etc.), sweeteners (e.g., sugars such as sucrose, isomerized sugar, lactose, maltose, glucose, fructose, invert sugar, starch syrup, powder starch syrup, reduced maltose syrup, honey, trehalose, palatinose, and D-xylose; sugar alcohols such as xylitol, sorbitol, maltitol, and erythritol; high-sweetness sweeteners such as sodium saccharin, cyclamate or salts thereof, potassium acesulfame, thaumatin, aspartame, sucralose, alitame, neotame, *stevia* extracts (e.g., stevioside), and *Momordica grosvenori* extract (e.g., mogroside)), flavors, and the like.

The edible metal salt is used to improve solubility of the thickening polysaccharide in water, or enhance thickening and gelling functions. The kind of edible metal salt is not particularly limited. Preferable examples include sodium salts (e.g., sodium chloride and sodium citrate), potassium salts (e.g., potassium chloride, potassium citrate, etc.), calcium salts (e.g., calcium chloride, calcium citrate, etc.), magnesium salts (e.g., magnesium chloride, etc.), and the like. When an edible metal salt is used, the proportion of the edible metal salt in the salivator of the present invention may be, for example, usually 0.1 to 15 mass %, and preferably 0.5 to 10 mass %, regardless of the form of the salivator (solid, semi-solid, or liquid form).

To produce the salivator in a form for intraoral use or oral intake, or stabilize the salivator, various carriers and additives pharmaceutically acceptable for oral administration may be incorporated (see, for example, a pharmacopeia, or the "Japanese Pharmaceutical Excipients Directory" (published by Yakuji Nippo, Limited)).

Examples of such carriers or additives include excipients such as monosaccharides (e.g., glucose, galactose, fructose, etc.), disaccharides (e.g., sucrose, saccharose, lactose, maltose, trehalose, etc.), sugar alcohols (e.g., xylitol, sorbitol, mannite, etc.), oligosaccharide, starches (e.g., corn starch, partially gelatinized starch, etc.), starch hydrolysates (e.g., dextrin, powdered starch syrup, etc.), cellulose or cellulose derivatives (e.g., crystalline cellulose, low-substituted hydroxypropyl cellulose, carmellose sodium, etc.), and talc; binders such as starch, gelatinized starch, gelatin, gum arabic, dextrin, methyl cellulose, ethyl cellulose, polyvinylpyrrolidone, hydroxypropyl methylcellulose, hydroxypropyl cellulose, and carboxymethyl cellulose or salts thereof; disintegrants such as calcium carbonate, crospovidone, starch, carboxymethyl cellulose calcium, low-substituted hydroxypropyl cellulose, carboxymethyl starch, crystalline cellulose, and agar; lubricants such as magnesium stearate, talc, polyethylene glycol, and silicic acid anhydride; suspending agents such as Polysorbate 80, polyoxyethylene hydrogenated castor oil, and Pluronic; coating agents such as saccharose, talc, precipitated calcium carbonate, gelatin, gum arabic, pullulan, carnauba wax, and hydroxypropylmethyl phthalate; corrigents such as saccharose, glucose, saccharin sodium, sorbitol, citric acid, and aspartame; and the like. As long as the effect of the present invention is not impaired, the following additives may also be used in addition to the above components: components usually acceptable as additives for pharmaceutical products, such as stabilizing agents, surfactants, plasticizers, capsule films, solubilizers, reducing agents, buffers, sweetening agents, bases, volatilization adjuvants, absorption enhancers, adsorbents, synergists, curing agents, antioxidants, brightening agents, perfumes, potency enhancers, coating agents, supports, prolonging agents, moistening agents, moisture regulators, fillers, defoaming agents, algefacients, eating stimulants, bonds, potentiators, chewable agents, antistatic agents, flavors, coloring agents, sugar-coating agents, tonicity agents, softeners, emulsifiers, combustion agents, adhesives, adhesion enhancers, viscosity modifiers, inflammation suppressants, exothermic agents, foaming agents, pH adjusters, skin protectants, flotation agents, dispersants, propellants, fragrances, antirust agents, desiccants, release control membranes, antiseptic agents, scavengers, preservatives, soothing agents, attractants, dissolving agents, dissolving adjuvants, solvents, liners, mold release agents, and fluidizers; components acceptable as food additives, such as sweeteners, coloring agents, preservatives, thickeners, gelling agents, starch adhesives, antioxidants, color formers, bleaching agents, antifungal agents, emulsifiers, leavening agents, seasoning agents, sour tastes, bitter tastes, gloss agents, gum bases, nutrition fortifiers, and agents for production; any components such as flavors. Components that have saliva secretion-promoting effects, such as spilanthol, may also be added.

(A-I-4) Form, Preparation Method, Function, Use, Etc., of the Salivator

The form of the salivator of the present invention is not limited as long as the salivator of the present invention comprises at least the enzymatically modified isoquercitrin alone, or the enzymatically modified isoquercitrin and a thickening polysaccharide. For example, the form of the salivator may be a solid (e.g., tablets, chewable agents, lozenges, pills, granules, powders (powdered medicine), dry syrups, films, stick-shaped preparations, etc.), a semi-solid (e.g., gels, pastes, etc.), a liquid (e.g., syrups, health drinks, liquids, emulsions, oils, sprays, etc.), and the like.

The salivator in a solid or semi-solid form is not particularly limited as long as it is in a form for use in the mouth (a form for intraoral use), or in a form for use by oral administration (a form for oral administration). The salivator may be, for example, in the form of a tablet, chewable agent, lozenge, pill, granule, powder (powdered medicine), dry syrup, film, stick-shaped preparation, gel, or paste. When used, the tablet, pill, granule, or powder (powdered medicine), dry syrup, etc., may be added to drinking water or a food or beverage; and dissolved or dispersed and mixed therein, and then administered (ingested).

The salivator of the present invention can be prepared in accordance with the form by known methods. For example, the salivator in the form of a powder (powdered medicine) or dry syrup can be prepared by powder-mixing enzymatically modified isoquercitrin alone, or enzymatically modified isoquercitrin and a thickening polysaccharide with an excipient. Alternatively, the salivator in the form of a powder can also be prepared by drying (e.g., spray-drying, freeze-drying, etc.) a liquid containing enzymatically modified isoquercitrin alone, or enzymatically modified isoquercitrin and a thickening polysaccharide. The salivator in the form of granules can be prepared by granulating the powder mixture. Alternatively, the salivator in the form of granules can also be prepared by spraying an aqueous solution of enzymatically modified isoquercitrin as a binder solution over a powder thickening polysaccharide. The salivator in the form of tablets can be prepared by tableting the powder or granular salivator into tablets using a tableting machine. The salivator in the form of a liquid can be prepared by adding enzymatically modified isoquercitrin alone, or enzymatically modified isoquercitrin and a thickening polysaccharide to a solvent (for example, ethanol or water, or a mixture thereof, preferably water such as purified water, ion exchange water, distilled water, or physiological saline); and preferably further mixing (for example, mixing by stirring). The salivator in the form of a liquid can be prepared as an emulsion or an oil by further adding a surfactant and/or a dispersant and a liposoluble solvent (for example, an oil solvent (e.g., a pharmaceutical oil solvent for dissolving a liposoluble medicament, edible oil, etc.), and preferably further mixing (for example, mixing by stirring) or performing homogenization treatment by using a high-pressure homogenizer etc. at the stage of preparing the salivator in the form of a liquid.

The gel salivator can be prepared by adding to a solvent (ethanol or water, or a mixture thereof, preferably water such as purified water, ion exchange water, or distilled water, or physiological saline) enzymatically modified isoquercitrin and a thickening polysaccharide that contributes to gelling, and heating until the thickening polysaccharide is homogeneously dissolved (dispersed) (the heating temperature depends on the polysaccharide to be added and may be, for example, 40 to 100° C.), followed by cooling. In this case, examples of polysaccharides that contribute to gelling include xanthan gum, locust bean gum, highly acylated gellan gum, gelatin, agar, and carrageenan. Alternatively, after enzymatically modified isoquercitrin and a thickening polysaccharide, which contributes to gelling, are added to a solvent (ethanol or water, or a mixture thereof, preferably purified water, ion exchange water, or distilled water, or physiological saline) and the resulting mixture is mixed and dissolved (dispersed) (at any appropriate temperature), the resulting solution may be gelled by adding an edible metal salt. In this case, examples of thickening polysaccharides that contribute to gelling include deacylated gellan gum, pectin, alginates, and carrageenan. The edible metal salt is not particularly limited. Preferable examples of edible metal salts include sodium salts (e.g., sodium chloride, sodium citrate, etc.), potassium salts (e.g., potassium chloride, potassium citrate, etc.), calcium salts (e.g., calcium chloride, calcium citrate, etc.), magnesium salts (e.g., magnesium chloride etc.), and the like. The edible metal salt, when used, is preferably incorporated into the composition for intraoral use or oral intake of the present invention in a proportion of 0.00001 to 15 mass %, and preferably 0.00002 to 10 mass %.

When the salivator is in the form of a liquid, the viscosity may be adjusted to 6 mPa·s or more, preferably 6 to 600 mPa·s, by using a thickener, if necessary.

The viscosity herein refers to the viscosity determined under the following measurement conditions using a fluid rheometer (for example, ARES-LS1 produced by TA Instruments).

Measurement Conditions

Measurement temperature: 20° C.
Geometry: cone-and-plate with a diameter of 50 mm and a
gap of 0.051 mm
Shear rate: 100 s$^{-1}$ The "viscosity" in this specification means the viscosity determined under these conditions.

The thickener is not particularly limited. Examples include thickening polysaccharides as described above; monosaccharides such as glucose and fructose; disaccharides such as sucrose, lactose, and trehalose; oligosaccharide consisting of three or more monosaccharides connected together; polysaccharides such as starch, inulin, and polydextrose; starch syrup; sugar alcohols such as sorbitol, mannitol, maltitol, erythritol, lactitol, xylitol, and glycerol; and mixtures of saccharides such as molasses, honey, fructose-glucose liquid sugar, reduced maltose syrup, reduced starch hydrolysate, and starch syrup (these may be collectively referred to as "saccharides"). These can be used alone, or in a combination of two or more. Preferably, the thickener is a thickening polysaccharide.

The salivator in the form of a liquid of the present invention can be provided in the form of a solution, spray, dropping, or ejection (including compositions for intraoral use, such as mouthwashes, liquid dentifrices, oral rinses, and oral sprays; and compositions for oral administration, such as syrups), or formulated into health drinks. The salivator in various forms as described above can be used in the state of being contained in various containers, such as bottles, pumps, sprays, tubes, cans, and jars.

The stick-shaped preparation can be directly applied to the lip or in the mouth, and particularly to the tooth surface and gum. The shape of the stick-shaped preparation is not particularly limited as long as it is in a solid form that can be dissolved by saliva after application. The preparation can be formed into a cylindrical, square-pillar, or like shape according to the purpose of use. The stick-shaped preparation is preferably accommodated in an easily portable, appropriately shaped plastic container in such a manner that the preparation can be pushed out. When used, an appropriate amount of the preparation can be pushed out of the accommodation container, and applied to the lip or in the mouth. Specifically, the preparation can be formed into the same shape as lipsticks, lip creams, etc.

The pH of the salivator of the present invention is not limited. In general, the pH is preferably in the range of 3 to 9, more preferably 3.5 to 8, and still more preferably 3.5 to 7.5. The salivator in the form of a solid or semi-solid form is usually preferably adjusted such that the salivator in the mouth after intake or administration has a pH in the range of 3 to 9. The pH in the mouth is preferably a pH in the range of 3.5 to 8, and more preferably a pH in the range of 3.5 to 7.5.

The salivator of the present invention is preferably prepared in such a manner that the amount of enzymatically modified isoquercitrin per intake is 0.1 to 250 mg, and more preferably to 0.4 to 100 mg. The salivator of the present invention can be used at any time when the amount of saliva decreases, or when an increase in saliva secretion is desired (when or before the mouth is dried). Accordingly, the number of administrations of the salivator of the present invention per day is not particularly limited. The salivator containing the above amount of enzymatically modified isoquercitrin can be administered once or several times a day, continuously or intermittently.

The salivator of the present invention has a saliva secretion-promoting function or saliva secretion-increasing function; and can be preferably used for subjects with reduced saliva secretion, or subjects who feel reduced saliva secretion. Examples of subjects with reduced saliva secretion include patients with saliva hyposecretion or xerostomia; or healthy persons whose mouth is in a dry state, for example, on exercising, bathing, or waking.

(A-I-5) Foods and Beverages Containing the Salivator

Foods and beverages having saliva secretion-promoting effects can be produced by incorporating the salivator of the present invention into foods or beverages. The timing of adding the salivator of the present invention to a food or beverage is not particularly limited. The salivator can be added, for example, in a step of producing a food or beverage, or immediately before eating the food or drinking the beverage after production. The food or beverage in which the salivator of the present invention is to be incorporated is not particularly limited. Examples include beverages such as milk beverages, lactobacillus beverages, drink yogurts, soft drinks, near-water beverages, isotonic drinks, carbonated beverages, fruit juice beverages, vegetable beverages, fruit and vegetable beverages, alcoholic beverages, powder beverages, concentrated drinks for dilution with water, coffee beverages, shiruko (sweet red-bean soup with pieces of rice cake) beverage, black tea beverages, green tea beverages, barley tea beverages, Koji (roasted green) tea beverages, genmai (brown rice) tea beverages, oolong tea beverages, hatomugi (adlay) tea beverages, soba (buckwheat) tea beverages, dattan soba (tartary buckwheat) tea beverages, pu'er tea beverages, and smoothie beverages; puddings such as custard pudding, milk pudding, chocolate pudding, soufflé pudding, and fruit juice-containing pudding; desserts such as jelly, gummi candy, Bavarian cream, mousse, yogurt, and multi-layer desserts; frozen desserts such as ice cream, ice milk, lacto ice, milk ice cream, fruit juice-containing ice cream, soft-serve ice cream, ice pops, sherbet, and frozen confections; gums (stick gum and sugar-coated gum granules) such as chewing gum and bubble gum; chocolates such as marble chocolate and like coating chocolates, strawberry chocolate, blueberry chocolate, melon chocolate, and like flavored chocolates; ramune (tablet candies); hard candies (including bonbons, butterballs, and marbles), soft candies (including caramel, nougat, gummi candy, and marshmallow), drops, taffy, and like caramels; baked confectioneries such as hard biscuits, cookies, macaroons, karinto (fried dough cake), okaki (cracker made from glutinous rice), and senbei (cracker made from regular rice) (the above items are confectioneries); soups such as miso soup, sumashi jiru (clear soup), consomme soup, potage soup, and vegetable soup; pickles such as asazuke (lightly pickled vegetables), soy sauce pickles, salt pickles, and miso pickles; sauces such as vinaigrette dressings, non-oil dressings, ketchup, gravy, and sauce; jams such as strawberry jam, blueberry jam, marmalade, apple jam, apricot jam, and preserves; dessert sauces such as fruit sauce, syrup, and maple syrup; fruit wines such as red wine; processed fruits such as candied cherries, apricots, apples, strawberries, and peaches; processed meats such as ham, sausage, and roast pork; ground marine products such as fish-meat ham, fish-meat sausage, ground fish meat, boiled fish paste, chikuwa (tubular fish cakes), hanpen (a cake of pounded fish), satsumaage (fried fish cakes), datemaki (mixed fish paste rolled omelet), and whale bacon; processed farm products such as konjac, azuki bean, soybean curd (tofu), and fermented soybean; dairy-fat products such as butter, margarine, cheese, and whipped cream; pastas such as udon (noodles made from buckwheat), hiyamugi (cold wheat noodles), somen (thin wheat noodles), soba (noodles made from buckwheat), Chinese soba noodles, spaghetti, macaroni, rice noodles, harusame (thin noodles made from bean starch), and wonton; baked goods such as breads, sweet buns, side dish breads, rolls, French breads, bagels, and croissants; flour-containing foods such as takoyaki (grilled dumplings with bits of octopus), okonomiyaki (grilled spicy pancakes with a wide variety of ingredients), crepe, shaomai (a steamed meat dumpling), jiaozi (a Chinese-style dumpling with minced pork and vegetable stuffing), spring roll, wonton, and pizza; cakes such as large pancakes, pancakes, cheesecakes, chiffon cakes, soufflé cakes, chocolate cakes, fruit cakes, tarts, pies, cream puffs, and eclairs; Japanese sweets such as ohagi (Japanese rice cake wrapped with a sweet bean paste), dumpling, bracken rice cake, kusamochi (a rice-flour dumpling mixed with mugwort), kudzu starch cake, manju (a steamed yeast bun with filling), yokan (azuki bean jelly), mizuyokan (soft, sweet jellied bean paste) anmitsu (mitsumame topped with a red bean jam), and glutinous rice-flour dumplings; grain staple foods such as cooked white rice, cooked brown rice, mugimeshi (rice cooked with barley), festive red rice, rice dumpling in bamboo leaves, and rice cakes; other various types of side dishes and processed foods such as fu (dried bread-like pieces of wheat gluten) and denbu (mashed and seasoned fish). The foods and beverages into which the salivator of the present invention is to be incorporated include concentrated liquid foods, enteral nutrients, thickened beverages, thickened liquid foods, nutrition supplement jelly, water-supplement jelly, semi-solid liquid food, liquid thickeners, and the like. The "liquid thickener" refers to a liquid preparation used by being added to a food or beverage before eating or drinking in order to thicken the food or beverage.

By promoting saliva secretion and increasing the amount of saliva secreted, the salivator of the present invention enables subjects with reduced salivation to easily swallow and chew. In this sense, the salivator of the present invention is also useful as a swallowing-assisting agent (a deglutition improver) or a chewing-assisting agent (or a mastication improver). In this invention, "swallowing" or "deglutition" refers to swallowing down an object in the mouth; and "chewing" or "mastication" refers to fragmenting an oral composition into small pieces in the mouth, or fully mixing an oral composition with saliva in the mouth while fragmenting the composition into small pieces. Finely cutting as used herein includes not only crunching an oral composition using the lower jaw and teeth, but also squashing an oral composition using the gums or tongue.

(A-II) Method for Promoting Saliva Secretion in Subject

As described above, the salivator of the present invention can promote saliva secretion not only in healthy subjects but also in subjects with reduced salivation, or subjects who feel reduced saliva secretion. Therefore, the present invention provides a method for producing saliva secretion in these subjects.

This method can be performed by applying the salivator of the present invention to the mouth of the subject, or by oral administration thereof. The application to the mouth can be suitably selected according to the form of the salivator. For example, when the salivator is in a liquid form such as a solution, spray, dropping, or ejection, application to the mouth may be, for example, mouth-rinsing, teeth-brushing, and gargle (gargling); or spraying into the mouth. When the salivator is in the form of a solid chewable agent (including gum), the application may be, for example, mastication (chewing). When the salivator is in a stick, gel, or paste (cream, ointment) form, for example, application to the mouth can be used. Oral administration can be performed by oral intake (administration) of the salivator in a liquid, semi-solid, or solid form (for example, a syrup, health drink, liquid, emulsion, oil, spray, gel, paste, tablet, chewable agent, lozenge, pill, granule, powder (powdered medicine), dry syrup, film, or stick-shaped preparation; or in the form of a syrup, drink, candy, jelly, gummi candy, edible film, or the like) according to the dosage form.

The timing of intake (administration) is not particularly limited. The salivator can be administered at any time when or before the mouth is dry. The amount of the salivator to be used is also not particularly limited. The salivator is preferably administered (ingested) in an amount such that the enzymatically modified isoquercitrin contained in the salivator is administered (ingested) in an amount of 0.1 to 250 mg, more preferably 0.4 to 100 mg. The number of times of administration of the salivator (number of times of intake) per day is not particularly limited. The salivator containing the enzymatically modified isoquercitrin can be administered (ingested) in the above amount once a day or several times, continuously or intermittently, as described above.

The subjects with reduced salivation, for whom the method of the present invention is preferably used, include, for example, persons with hyposalivation or xerostomia; or healthy persons whose mouth is in a dry state on exercising, bathing, waking, etc. Examples of the method for diagnosing reduction in saliva secretion include (1) methods for measuring the amount of saliva produced at rest (the spitting method, the cotton-roll method), (2) a method for measuring the amount of saliva secreted upon stimulation (the Saxon method), (3) methods for measuring the degree of oral mucosa moisture (the Periotron method, the filter paper method, an intraoral moisture meter), (4) methods for measuring the physical properties of saliva (viscosity test, spinnability test), and (5) questionnaire methods. Whether saliva secretion in a subject is reduced or not can be evaluated by using any one of these methods, or a combination of two or more of these methods.

(B-I) Additive for Composition for Intraoral Use or Oral Intake

The additive for compositions for intraoral use or oral intake (hereinafter also simply referred to "the additive of the present invention" is characterized by containing enzymatically modified isoquercitrin and a thickening polysaccharide.

(B-I-1) Enzymatically Modified Isoquercitrin

The enzymatically modified isoquercitrin used in the present invention is as explained above in (A-I-1), the disclosure of which is herein incorporated by reference in its entirety.

(B-I-2) Thickening Polysaccharide

The thickening polysaccharide used in the present invention is an edible thickening polysaccharide approved for use in foods and beverages or pharmaceutical products for oral administration. The thickening polysaccharide is as explained above in (A-I-2), whose disclosure is herein incorporated by reference in its entirety.

The proportion of the thickening polysaccharide contained in the additive of the present invention may vary according to the form of the additive. For example, when the additive is in the form of a powder, granules, or tablets, the proportion of the thickening polysaccharide can be usually suitably selected from the range of 1 mass % or more and less than 100 mass %, preferably in the range of 3 to 90 mass %, and more preferably 5 to 80 mass %. When the additive is in the form of a paste or liquid, the proportion of the thickening polysaccharide can be usually suitably selected from the range of 0.1 to 10 mass %, preferably 0.2 to 8 mass %, and more preferably 0.3 to 6 mass %.

The proportion of the thickening polysaccharide to the enzymatically modified isoquercitrin in the additive of the present invention can be usually selected from the range of 0.2 to 500 parts by mass, per part by mass of the enzymatically modified isoquercitrin (in terms of rutin; the same applies hereinafter). The proportion of the thickening polysaccharide to the enzymatically modified isoquercitrin in the additive of the present invention can be selected and adjusted according to the form of the oral composition prepared by addition. For example, when the additive of the present invention is an additive for preparing a sol composition for oral intake, the proportion of the thickening polysaccharide may be in the range of 0.2 to 400 parts by mass, preferably 0.3 to 350 parts by mass, and more preferably 0.4 to 300 parts by mass, per part by mass of the enzymatically modified isoquercitrin. When the additive of the present invention is an additive for preparing a gel composition for oral administration, the proportion of the thickening polysaccharide is in the range of 1 to 500 parts by mass, preferably 2 to 450 parts by mass, and more preferably 2.5 to 350 parts by mass, per part by mass of the enzymatically modified isoquercitrin. When the additive of the present invention is an additive for preparing a food or beverage prepared by processing cereal grains (a processed grain food or beverage), the proportion of the thickening polysaccharide may be, for example, 0.01 to 3000 parts by mass, preferably 0.05 to 2000 parts by mass, and more preferably 0.1 to 1200 parts by mass, per part by mass of the enzymatically modified isoquercitrin.

(B-I-3) Other Components

As long as the effect of the present invention is not impaired, the additive of the present invention may contain any edible components in addition to the above components.

Examples of edible components include, but are not limited to, those mentioned above in (A-I-3), the disclosure of which, including the disclosure regarding the proportion of edible metal salts, is herein incorporated by reference in its entirety.

(B-I-4) Form, Preparation Method, Effect, Use, Etc., of the Additive

The form of the additive of the present invention is not limited, as long as the additive comprises at least the enzymatically modified isoquercitrin and thickening polysaccharide. For example, a solid form, a paste form, and a liquid form can be used. Preferably, the form of the additive is a solid form, such as a powder, granules, or tablets; or a liquid form. The additive is more preferably in the form of granules because of its excellent solubility in water.

The additive of the present invention can be prepared according to the form in a usual manner. For example, the additive in the form of a powder can be prepared by powder-mixing enzymatically modified isoquercitrin and a thickening polysaccharide with an excipient. Alternatively, the additive in the form of a powder can also be prepared by drying (e.g., spray-drying, freeze-drying) a liquid containing enzymatically modified isoquercitrin and a thickening polysaccharide. The additive in the form of granules can be prepared by granulating the powder mixture. Alternatively, the additive in the form of granules can also be prepared by spraying enzymatically modified isoquercitrin as a binder solution over a powder-thickening polysaccharide. The additive in the form of tablets can be prepared by forming the powdery or granular additive into tablets using a tableting machine. The liquid additive can be prepared by adding enzymatically modified isoquercitrin and a thickening polysaccharide to a solvent (preferably water).

When water or the composition for intraoral use or oral intake containing water (e.g., a liquid composition for intraoral use or oral intake) is ingested or administered, the additive of the present invention is usually used by being added to the target composition for intraoral use or oral intake. The target composition for intraoral use or oral intake is water itself, or formulated in such a manner that the composition contains at least a predetermined amount of water. Therefore, when the additive of the present invention is added and mixed by stirring, the viscosity increases so that the composition becomes a sol or gel.

The temperature of the target composition for intraoral use or oral intake when the additive of the present invention is added and mixed may be, for example, a temperature at which the additive of the present invention is dissolved or dispersed, and a thickening polysaccharide contained in the additive is thereby hydrated and swells. This temperature may vary depending on the type of thickening polysaccharide, and can be suitably set in the range of 1 to 100° C.

The amount of the additive of the present invention added to the target composition for intraoral use or oral intake can be suitably adjusted according to the kind, water content, purpose, and use of the target composition for intraoral use or oral intake. For example, the additive is preferably added in a proportion such that the enzymatically modified isoquercitrin content of the composition for intraoral use or oral intake after incorporating the additive of the present invention therein is 0.0005 to 1 mass %. The enzymatically modified isoquercitrin content of the composition for intraoral use or oral intake is preferably 0.001 to 0.7 mass %, and more preferably 0.0015 to 0.5 mass %.

When the target composition for intraoral use or oral intake is a food or beverage prepared by processing cereal grains (a processed grain food or beverage), the additive is particularly preferably added in a proportion such that the enzymatically modified isoquercitrin content of the composition for oral intake after incorporating the additive of the present invention therein is 0.003 to 0.5 mass %. The enzymatically modified isoquercitrin content of the processed grain food or beverage is preferably 0.005 to 0.45 mass %, and more preferably 0.0065 to 0.4 mass %.

The additive of the present invention can be used for imparting a saliva secretion-promoting effect to the target composition for intraoral use or oral intake. In other words, the additive of the present invention is used to prepare a composition for intraoral use or oral intake having a salivation-promoting effect. In this sense, the additive of the present invention can be called a salivator. The "salivator" has the action of increasing the amount of saliva secretion. In the present invention, as stated above, the "salivator" imparts the effect of increasing the amount of saliva secretion (salivation-promoting action) to the composition for intraoral use or oral intake.

The additive of the present invention can be used to impart an easy-to-swallow property to the target composition for intraoral use or oral intake. In other words, the additive of the present invention is used to prepare a composition for intraoral use or oral intake that can be easily swallowed. In this sense, the additive of the present invention can be called a swallowing-assisting agent (or a deglutition-improving agent). Further, the additive of the present invention can be used to impart an easy-to-chew property to the composition for intraoral use or oral intake. In other words, the additive of the present invention is used for preparing a composition for intraoral use or oral intake that can be easily chewed. In this sense, the additive of the present invention can be called a chewing-assisting agent (or a mastication-improving agent).

The concepts or definitions of "swallowing" and "chewing" are as explained above in (A-I-5), the disclosure of which is herein incorporated by reference herein in its entirety.

(B-I-5) Composition for Intraoral Use or Oral Ingestion to which the Additive of the Present Invention is Added The composition for intraoral use to which the additive of the present invention is added is foods or beverages, or pharmaceutical products for intraoral use, which are ingested or taken (administered) from the mouth or remain in the mouth. Examples include foods and beverages, such as gums, gummi candies, films, and tablets (e.g., lozenges); and pharmaceutical products for intraoral use, such as mouthwashes, toothpastes, films, tablets (e.g., lozenges). The target composition for oral intake to which the additive of the present invention is added is foods or beverages, or pharmaceutical products for oral administration, which are ingested or taken (administered) from the mouth. The composition for intraoral use and the composition for oral intake are different in that the composition for intraoral use refers to compositions used in the state of residing in the mouth for a certain period of time (including compositions that are swallowed, and compositions that are not swallowed), whereas the composition for oral intake is usually swallowed without residing in the mouth except for the time necessary for chewing. However, the composition for intraoral use and the composition for oral intake are not necessarily strictly distinguished from each other, and may partially overlap. To make a distinction from the composition for oral intake according to the present invention described later, the compositions for intraoral use or oral intake to which the additive of the present invention is to be added may also be referred to as the "target compositions for intraoral use or oral intake," and the foods or beverages or pharmaceutical products for intraoral use or oral intake to which the additive of the present invention is to be added may also be referred to as the "target foods or beverages" and "target pharmaceutical products for intraoral use or oral intake."

Specific examples of the target foods or beverages include beverages such as water (including mineral water), soft drinks (e.g., tea-based beverages, fruit beverages, vegetable beverages, coffee beverages, cocoa beverages, sports supplement drinks, carbonated drinks, lactic beverages, soy milks, soy milk beverages, isotonic drinks, etc.), milk products (e.g., cow's milk, lactic acid bacteria beverages, etc.); soup products such as soup, miso soup, shiruko (sweet red bean soup with rice cake), and amazake (sweet drink made from fermented rice); confectionery products (including paste or gel confectionery, liquefied confectionery products (e.g., minced foods, paste foods, and weaning foods)); nutritional supplement beverages and foods (including nutritional supplement beverages or foods in paste or gel form, liquid nutritional supplement beverages and foods (e.g., minced foods, paste foods, and weaning foods)); staple foods (including, for example, cooked rice foods, noodles, baked goods, etc., liquid staple foods (e.g., minced foods, paste foods, and weaning foods)); side dishes (including liquefied side dishes (e.g., minced foods, paste foods, and weaning foods)); concentrated liquid foods; enteral nutrients (orally administered or orally ingested); and the like. The above confectioneries, nutritional supplement foods and beverages, staple foods, side dishes, etc., include processed grain foods and beverages obtained by processing cereal grains. The minced foods herein refer to foods obtained by fragmenting food materials by a cutter, a mixer, or the like. The paste foods refer to foods obtained by forming food materials into a paste. There is no strict distinction between minced foods and paste foods. Both are adjusted to have high fluidity to allow persons with difficulty in swallowing or chewing etc. to easily enjoy eating. The fluidity of minced foods and paste foods can be adjusted by adding water, if necessary.

Examples of the processed grain foods include foods and beverages obtained by processing cereal grains, such as grain (barley, wheat), Japanese barnyard millet, foxtail millet, rice, buckwheat, beans (e.g., soybean), and corns. Examples include, but are not limited to, confectioneries (for example, baked confectioneries such as cookies, biscuits, crackers, doughnuts, rusks, cakes (including pancakes), madeleines, macaroons, pies, and cream puffs), fried confectionaries, and steamed confectioneries); cooked rice products; noodles (e.g., udon (noodles made from wheat flour), buckwheat noodles, ramen noodles, harusame (starch noodle), macaroni, and wonton); baked goods (including Chinese steamed buns and pizzas); wrapped foods (e.g., jiaozi (a Chinese-style dumpling with minced pork and vegetable stuffing), shaomai (a steamed meat dumpling), wonton, and spring roll) and wrappers thereof; premix powders for producing flour-containing foods, such as pancake mix, mix for takoyaki (grilled dumplings with bits of octopus), mix for okonomiyaki (grilled spicy pancakes with a wide variety of ingredients), crepe mix, batter mix) (for example, pancake mix, takoyaki mix, okonomiyaki mix, crepe mix, and batter mix), cornflakes, and the like. Many of these processed grain foods or beverages have a low water content, tend to be dry, and have difficulty in forming an alimentary bolus; and become sticky when water is added, thus poorly melting in the mouth or becoming difficult to swallow. In particular, many cooked rice foods, and confectioneries, noodles, and baked goods mainly comprising flour have physical properties that make them difficult for persons with reduced chewing function or reduced swallowing function to swallow. When the additive of the present invention is applied to gain processed foods and beverages having such physical properties, melt-in-the-mouth properties of the processed grain products can be enhanced. Further, when such foods are eaten, a feeling of cohesiveness in the mouth can be obtained and/or a feeling of adhesion to the pharynx can be reduced. Therefore, processed grain foods and beverages that are easy to swallow can be prepared.

The target pharmaceutical products for intraoral use or oral intake is not particularly limited, as long as it is used in the mouth or orally administered. Examples include powders (powdered medicine), granules, tablets (including lozenges and chewable agents), pills, capsules, films, and liquids (health drinks).

When the additive of the present invention is incorporated into the target composition for intraoral use or oral intake, the composition for intraoral use or oral intake preferably contains at least a predetermined amount of water. The water content of the target composition for intraoral use or oral intake is preferably 60 mass % or more, preferably 70 mass % or more, and more preferably 80 mass % or more. Accordingly, when the water content of the target composition for intraoral use or oral intake (foods and beverages, pharmaceutical products for intraoral use or oral administration) is less than 60 mass %, the water content of the composition for intraoral use or oral intake is preferably adjusted to the range described above before the additive of the present invention is added. For example, when the target composition for intraoral use or oral intake is a pharmaceutical preparation in the form of a powder or granules, a method comprising adding water to achieve a water content of 60 mass % or more and dispersing such a preparation in water can be used.

(B-II) Composition for Intraoral Use or Oral Ingestion and Production Method Therefor The present invention provides a composition for intraoral use or oral intake comprising enzymatically modified isoquercitrin and a thickening polysaccharide. The composition for intraoral use or oral intake includes a composition for intraoral use or oral intake comprising the additive of the present invention described above. The composition for intraoral use of the present invention is a food or beverage or a pharmaceutical product for intraoral use that is ingested or taken (administered) from the mouth and is retained in the mouth. Examples include foods and beverages, such as gums, films, and tablets; and pharmaceutical products for intraoral use, such as mouthwashes, toothpastes, films, and tablets. The composition for oral administration of the present invention is not limited as long as it can be orally ingested or administered. Examples of the composition include foods and beverages and pharmaceutical products for oral administration.

The composition for intraoral use or oral intake of the present invention can be prepared by using enzymatically modified isoquercitrin and a thickening polysaccharide, preferably using the additive of the present invention described above.

The proportion of enzymatically modified isoquercitrin in the composition for intraoral use or oral intake of the present invention is not particularly limited as long as the effect of the present invention is provided. The proportion may be usually, for example, in the range of 0.0005 to 1 mass %, preferably 0.001 to 0.7 mass %, more preferably 0.0015 to 0.5 mass %. When the target composition for intraoral use or oral intake is a food or beverage prepared by processing cereal grains (a processed grain food or beverage), the proportion of the enzymatically modified isoquercitrin in the oral composition of the present invention is particularly preferably 0.003 to 0.5 mass %, more preferably 0.005 to 0.45 mass %, and even more preferably 0.0065 to 0.4 mass %.

The proportion of the thickening polysaccharide in the composition for intraoral use or oral intake of the present invention may be, for example, in the range of 0.2 to 500 parts by mass per part by mass of the enzymatically modified isoquercitrin contained in the composition for intraoral use or oral intake of the present invention. The proportion of the thickening polysaccharide to the enzymatically modified isoquercitrin contained in the composition for intraoral use or oral intake of the present invention can be selected and adjusted according to the type of composition for intraoral use or oral intake to which the thickening polysaccharide is added. For example, when the composition for intraoral use or oral intake of the present invention is a sol composition for intraoral use or oral intake, the proportion of the thickening polysaccharide may be, for example, 0.2 to 400 parts by mass, preferably 0.3 to 350 parts by mass, and more preferably 0.4 to 300 parts by mass, per part by mass of the enzymatically modified isoquercitrin contained in the composition for intraoral use or oral intake. When the composition for intraoral use or oral intake of the present invention is a gel composition for intraoral use or oral intake, the proportion of the thickening polysaccharide may be, for example, 1 to 500 parts by mass, preferably 2 to 450 parts by mass, and more preferably 2.5 to 350 parts by mass, per part by mass of the enzymatically modified isoquercitrin contained in the composition for intraoral use or oral intake. When the composition for intraoral use or oral intake of the present invention is a processed grain food or beverage, the proportion of the thickening polysaccharide may be, for example, 0.01 to 3000 parts by mass, preferably 0.05 to 2000 parts by mass, and more preferably 0.1 to 12000 parts by mass, per part by mass of the enzymatically modified isoquercitrin.

As long as the above conditions are met, there is no particular limitation. The proportion of the thickening polysaccharide may be usually, for example, in the range of 0.01 to 10 mass %, preferably 0.02 to 8 mass %, and more preferably 0.03 to 6 mass %, per 100 mass % of the composition for intraoral use or oral intake of the present invention.

The composition for intraoral use or oral intake of the present invention can be prepared by adding enzymatically modified isoquercitrin and a thickening polysaccharide to the target composition for intraoral use or oral intake of the present invention before, preferably immediately before, ingesting or taking (administering) the composition. The composition for intraoral use or oral intake of the present invention can be prepared by adding enzymatically modified isoquercitrin and a thickening polysaccharide to a target composition for intraoral use or oral intake and mixing by stirring. After mixing by stirring, if necessary, the resulting product is allowed to stand or cooled to solidify the product into a gel, thus preparing the composition for intraoral use or oral intake of the present invention. As the enzymatically modified isoquercitrin and thickening polysaccharide, the additive of the present invention described above can be conveniently used.

The target composition for intraoral use or oral intake include, for example, those disclosed above in (B-I-5). The disclosure is herein incorporated by reference. When the water content of the target composition for intraoral use or oral intake is less than 60 mass %, the water content of the target composition for intraoral use or oral intake is preferably adjusted to 60 mass % or more by, for example, adding water.

The temperature conditions for adding enzymatically modified isoquercitrin and a thickening polysaccharide (or the additive of the present invention) to the composition for intraoral use or oral intake, or the temperature conditions for mixing by stirring may be any temperature at which the enzymatically modified isoquercitrin and thickening polysaccharide can be dissolved or dispersed in the target composition for intraoral use or oral intake.

Among thickening polysaccharides, deacylated gellan gum, carrageenan, pectin, alginates, etc., have the property of increasing viscosity or gelling in the presence of a soluble metal salt. Therefore, when such a thickening polysaccharide is used, a soluble metal salt is preferably used together. The soluble metal salt to be used is not limited, and preferable examples include sodium salts (e.g., sodium chloride, sodium citrate, etc.), potassium salts (e.g., potassium chloride, potassium citrate, etc.), calcium salts (e.g., calcium chloride, calcium citrate, etc.), magnesium salts (e.g., magnesium chloride etc.), and the like. When an edible metal salt is used, a preferable proportion of the edible metal salt in the composition for intraoral use or oral intake of the present invention is usually 0.00001 to 15 mass %, and preferably 0.00002 to 10 mass %.

The manner of mixing by stirring is not particularly limited. For example, mixing may be performed by stirring with a chopstick, a spoon, or a fork; or by stirring using a stirring tool, such as a household mixer, a food processor, a rotary beater, a blender, a cooking cutter, or a propeller stirrer.

The composition for intraoral use or oral intake of the present invention thus obtained can be prepared in the form of a gel or a sol having the predetermined physical properties.

The "gel" referred to herein specifically means that when the product is allowed to stand at a product temperature of 20° C. for 1 to 2 minutes, its shape is retained and the product does not flow under its own weight; i.e., its shape does not change between the state 1 minute after being allowed to stand at a product temperature of 20° C., and the state 2 minutes after being allowed to stand at 20° C. The "sol" means that when allowed to stand at a product temperature of 20° C., the product flows under its own weight, and its shape is not retained; or its shape changes between the state 1 minute after being allowed to stand at a product temperature of 20° C., and the state 2 minutes after being allowed to stand at 20° C. These all refer to the state under standard atmospheric pressure (1 atm) conditions.

When the composition for intraoral use or oral intake of the present invention is in the form of a gel, the composition for intraoral use or oral intake preferably has a fracture strain of 0.3 to 0.8, more preferably 0.4 to 0.8, and still more preferably 0.45 to 0.75, as determined at a product temperature of 20° C. under standard atmospheric pressure conditions.

The "fracture strain" referred to herein can be determined by the following measurement method.

Method for Determining the Fracture Strain (a) As a test sample, a composition for intraoral use or oral intake (a test sample) (product temperature: 20° C.) having a cylindrical shape with a diameter of 20 mm and a height of 10 mm is prepared.

(b) Using a texture analyzer (TA-XT-2i (produced by Stable Micro Systems) texture analyzer), the test sample is compressed. The compression is performed at a rate of 10 mm/s using a jig having a diameter of 100 mm.

(c) The fracture point is determined from a "stress-strain curve" obtained by the compression, and the fracture strain is calculated by the following formula.

$$\text{Fracture strain}=A/B \qquad [\text{Math. 2}]$$

A: Distance (mm) from the position where the jig first comes into contact with the test sample (the upper surface of the test sample) to the point where the sample is broken by being contacted and compressed with the jig (fracture point).
B: Height of the test sample (=10 mm)

When the fracture strain of the gel composition for intraoral use or oral intake has a fracture strain of 0.3 to 0.8, preferably 0.4 to 0.8, and more preferably 0.45 to 0.75, the oral composition fragmented by chewing in the mouth is appropriately gathered into a mass (provides a feeling of cohesiveness), thus forming an alimentary bolus that can be easily chewed and swallowed even by persons with reduced chewing function or reduced swallowing function. If the fracture strain exceeds 0.8, time is required to fragment the oral composition in the mouth, and difficulty in swallowing may occur.

The gel composition for intraoral use or oral intake comprising both enzymatically modified isoquercitrin and a thickening polysaccharide tends to have a higher saliva secretion-promoting effect as the gel composition for intraoral use or oral intake has a smaller fracture strain. Specifically, when the gel food or beverage (20° C.) has a fracture strain of 0.3 to 0.8, preferably 0.4 to 0.8, and more preferably 0.45 to 0.75, a particularly remarkable salivation-promoting effect is provided.

When the composition for intraoral use or oral intake of the present invention is in the form of a gel, the composition for intraoral use or oral intake preferably has a "hardness" of 500,000 N/m$^2$ or less, preferably 500 to 400,000 N/m$^2$, and more preferably 500 to 250,000 N/m$^2$, as measured at a product temperature of 20° C. under standard atmospheric pressure conditions. The "hardness" can be determined according to the Universal Design Food Voluntary Standard, second edition (the Japan Care Food Conference). More specifically, the hardness can be determined by the following measurement method.

Method for Measuring the Hardness

A test sample is placed in a container having a diameter of 40 mm and a height of 20 mm. Using a texture analyzer (TA-XT-2i (produced by Stable Micro Systems) texture analyzer) and a resin plunger having a diameter of 20 mm and a height of 8 mm, compression measurement is performed twice at a compression speed of 10 mm/sec with a clearance of 5 mm. The maximum stress at the time of the first compression is defined as "hardness" (N/m$^2$).

In particular, when the "hardness" is in the range of 500 to 500,000 N/m$^2$, preferably 500 to 250,000 N/m$^2$, the obtained oral composition is easy to chew or swallow, even for persons with reduced chewing function.

When the composition for intraoral use or oral intake of the present invention is in the form of a sol, the composition for intraoral use or oral intake preferably has a viscosity of 0.006 Pa·s or more, more preferably 0.006 to 0.6 Pa·s, and still more preferably 0.008 to 0.4 Pa·s, at a shear rate of 100 s$^{-1}$. The "viscosity" referred to herein can be measured by using a jig (made of resin) with corn-and-plate geometry having a diameter of 50 mm, and reading the viscosity value at a measurement temperature of the sample (product temperature) of 20° C. and at a shear rate of 100 s$^{-1}$. ARES-LS1 (produced by TA Instruments) can be used as the measuring apparatus.

The composition for intraoral use or oral intake thus obtained, which contains a thickening polysaccharide in addition to enzymatically modified isoquercitrin, has an excellent salivation-promoting function, as compared with oral compositions not containing a thickening polysaccharide, as shown in the Experimental Examples described below. Therefore, the composition for intraoral use or oral intake can be provided as a food or beverage or a pharmaceutical product for intraoral use or oral administration suitable for persons with reduced saliva secretion function. The composition for intraoral use or oral intake of the present invention, which contains a thickening polysaccharide in addition to enzymatically modified isoquercitrin, has an excellent easy-to-swallow property and easy-to-chew property, as compared with compositions for intraoral use or oral intake not containing a thickening polysaccharide. Therefore, the composition for intraoral use or oral intake of the present invention can be provided as a food or beverage that can be suitably ingested by persons with reduced chewing function and/or persons with reduced swallowing function, or as a pharmaceutical product for intraoral use or oral administration that can be suitably taken by persons with reduced chewing function and/or persons with reduced swallowing function.

When the composition for intraoral use or oral intake of the present invention is a processed grain food or beverage, the timing of adding the composition is not particularly limited as long as the composition contains enzymatically modified isoquercitrin and a thickening polysaccharide before ingestion or administration (taking). For example, when the composition for intraoral use or oral intake of the present invention is a baked confectionery product, such as cookies, enzymatically modified isoquercitrin and a thickening polysaccharide can be added to a dough before baking to provide a processed grain food or beverage with improved melt-in-the-mouth sensation.

EXAMPLES

The following Experimental Examples and Formulation Examples are provided to better clarify the constitution and effects of the present invention. However, the present invention is by no means affected by these Experimental Examples etc.

Experimental Example 1

(1) Preparation of Test Samples

An enzymatically modified isoquercitrin preparation (SAN EMIQ® No. 1: produced by San-Ei Gen F.F.I.)

(containing enzymatically modified isoquercitrin in a proportion of 10 mass % in terms of α-glucosyl isoquercitrin (as rutin), and further containing dextrin as another component); α-glucosylrutin (αG rutin) (produced by Toyo Sugar Refining Co., Ltd.); and quercetin (produced by LKT Laboratories, Inc.) were used as test substances. These test substances were individually dissolved in ion exchange water to prepare aqueous solutions of the test substances at the various concentrations shown in Table 1 (test samples).

Table 1 shows the contents of the enzymatically modified isoquercitrin preparation and αG rutin in terms of rutin (molarity) and the molar concentration of quercetin, in addition to the test substance content of each test sample (mass %).

TABLE 1

| Content (molarity) in terms of rutin or molarity of quercetin (μM) | Enzymatically modified isoquercitrin preparation (α-glucosyl isoquercitrin content (in terms of rutin)) (mass %) | αG rutin (content in terms of rutin) (mass %) | Quercetin (mass %) |
|---|---|---|---|
| 25 μM | 0.0153 (0.00153) | — | — |
| 75 μM | 0.0458 (0.00458) | 0.0116 | 0.0023 |
| 150 μM | 0.0915 (0.00915) | 0.0232 | 0.0045 |
| 750 μM | 0.4575 (0.04575) | 0.1161 | 0.0227 |
| 3750 μM | 2.2875 (0.22875) | 0.5805 | 0.1133 |

The molarity of quercetin and the content of rutin contained in the enzymatically modified isoquercitrin and αG rutin (both are quercetin glycosides) were calculated by the following method.

Quantification of Quercetin (Molarity)

The quantity of quercetin (molarity) was calculated with the molecular weight of quercetin being defined as 302.

Amount (Molarity) of Enzymatically Modified Isoquercitrin and αG Rutin in Terms of Rutin The quantity of enzymatically modified isoquercitrin and αG rutin (molarity) was determined according to the quantification method described on the "Enzymatically Modified Isoquercitrin" page in the Specifications and Standards for Food Additives, 8th Edition (The Ministry of Health, Labour and Welfare, Japan). The details are as described above.

For example, when the α-glucosyl isoquercitrin content of the enzymatically modified isoquercitrin preparation (sample A) (in terms of rutin $((C_{27}H_{30}O_{16}))$ calculated by the above formula [Math. 1] is 10 mass %, 6100 g of the enzymatically modified isoquercitrin preparation (sample A) ($610 \times (100/10)=6100$) (610 is the molecular weight of rutin) corresponds to 1 mol of enzymatically modified isoquercitrin. Accordingly, in the above case, for example, to achieve a molarity of enzymatically modified isoquercitrin in an aqueous solution of 75 μM ($75 \times 10^{-6}$ mol/L), 0.4575 g ($6100$ g/mol$\times 75 \times 10^{-6}$ mol) of the enzymatically modified isoquercitrin preparation (sample A) must be dissolved (or dispersed) in 1 L of water.

(2) Evaluation of Salivation-Promoting Effect

Using 3 healthy persons (males, average age: 31.3 years old) as panelists, the salivation-promoting effect of the test samples prepared above was evaluated. Persons whose circadian variation of saliva secretion is relatively similar were selected as the panelists from candidates.

The evaluation was performed using 15 g of each test sample per test according to the following method. As a blank, a test was performed in the same manner using 15 g of water in place of the test samples.

(i) After 15 g of each sample is placed in the mouth and retained for 5 seconds, the sample is swallowed at one time.
(ii) After 5 seconds, absorbent cotton (37.5 mm×37.5 mm×4 mm) is placed under (the back of) the tongue, and retained for 2 minutes.
(iii) The absorbent cotton is removed from under the tongue, and the weight (g) of the cotton is measured. This weight is compared with the weight of the absorbent cotton before being placed in the mouth to calculate the difference in weight.

The above test was performed using the same test sample twice per panelist, and the average was calculated. Based on the average of each panelist, the average and standard deviation of all of the panelists were calculated.

(3) Evaluation Results

Table 2 and FIG. 1 show the evaluation results (the average of 3 panelists). The results are shown as numerical values (relative values) standardized by setting the saliva secretion amount obtained by using the blank (water) as 1.

TABLE 2

| Test sample | Amount of salivation (standardized with water) | Standard deviation |
|---|---|---|
| 25 μM enzymatically modified isoquercitrin aqueous solution | 1.209 | 0.443 |
| 75 μM enzymatically modified isoquercitrin aqueous solution | 1.794 | 0.522 |
| 75 μM αG rutin aqueous solution | 0.910 | 0.356 |
| 75 μM quercetin aqueous solution | 0.989 | 0.388 |
| 150 μM enzymatically modified isoquercitrin aqueous solution | 1.907 | 0.117 |
| 150 μM αG rutin aqueous solution | 0.841 | 0.093 |
| 150 μM quercetin aqueous solution | 0.826 | 0.133 |
| 750 μM enzymatically modified isoquercitrin aqueous solution | 2.259 | 0.162 |
| 750 μM αG rutin aqueous solution | 0.872 | 0.232 |
| 750 μM quercetin aqueous solution | 1.032 | 0.139 |
| 3750 μM enzymatically modified isoquercitrin aqueous solution | 2.034 | 0.170 |
| 3750 μM αG rutin aqueous solution | 0.932 | 0.123 |
| 3750 μM quercetin aqueous solution | 1.132 | 0.276 |

As is clear from this result, the enzymatically modified isoquercitrin in a concentration range of 25 to 750 μM exhibits a salivation-promoting (increasing) effect in a molarity-dependent manner. In particular, the effect is provided immediately after placing the enzymatically modified isoquercitrin in the mouth, or after swallowing the enzymatically modified isoquercitrin. This effect was not observed in quercetin itself or αG rutin, which is also a quercetin glycoside, like enzymatically modified isoquercitrin; this effect is specific to enzymatically modified isoquercitrin.

The above results clearly show that oral intake of samples containing enzymatically modified isoquercitrin (intraoral use, oral intake) can significantly increase saliva secretion.

Experimental Example 2

Xanthan gum was added as a thickening polysaccharide to the test samples of Experimental Example 1 (aqueous solutions of enzymatically modified isoquercitrin, αG rutin, and quercetin) to thicken the samples. The resulting compositions were evaluated for salivation-promoting effect in the same manner as in Experimental Example 1 to investigate whether containing or not containing xanthan gum (being thickened or not being thickened) makes a difference in the effect.

(1) Preparation of Test Samples

Test substances (enzymatically modified isoquercitrin preparation, αG rutin, and quercetin) were dissolved in drinking water, and adjusted so that the rutin content (molarity) of the structure of each compound was 150 μM (see Table 1). Further, xanthan gum was added to the aqueous solutions, so that the content thereof was 0.1 mass %, thus thickening the solutions. For comparison, xanthan gum-free aqueous solutions (an aqueous enzymatically modified isoquercitrin solution, an aqueous αG rutin solution, an aqueous quercetin solution) at a concentration of 150 μM in terms of rutin were prepared in the same manner as in Experimental Example 1.

The viscosity of each sample was measured using a fluid rheometer (ARES-LS1, produced by TA Instrument) under the following measurement conditions.

Measurement Conditions

Measurement temperature: 20° C.
Geometry: corn-and-plate with a diameter of 50 mm and a gap of 0.05 mm
Shear rate: $100 \text{ s}^{-1}$.

(2) Evaluation of Salivation-Promoting Effect and Results Thereof

Figure 2:
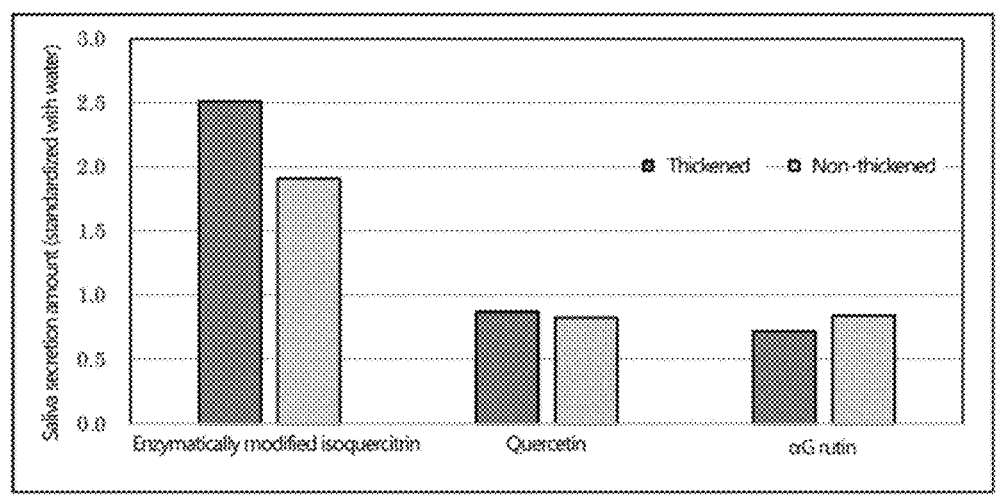
FIG. 2 is a graph showing the measurement results of salivation-promoting effects in Experimental Example 2.

The salivation-promoting effect of each test sample prepared above was evaluated in the same manner as in Experimental Example 1 (the panelists were also the same). Table 3 and FIG. 2 show the evaluation results (the average of 3 panelists).

All of the thickened samples had a viscosity of 20 mPa·s, and all of the non-thickened samples had a viscosity of 1 mPa·s (20° C.)

TABLE 3

| | | α-Glucosyl isoquercitrin content (content in terms of rutin) | Amount of salivation (standardized with water) | Standard deviation |
|---|---|---|---|---|
| Thickened | Enzymatically modified isoquercitrin | 150 μM | 2.511 | 0.904 |
| | αG rutin | 150 μM | 0.719 | 0.167 |
| | Quercetin | 150 μM | 0.868 | 0.109 |
| Non-thickened | Enzymatically modified isoquercitrin | 150 μM | 1.907 | 0.117 |
| | αG rutin | 150 μM | 0.841 | 0.093 |
| | Quercetin | 150 μM | 0.826 | 0.133 |

As is clear from these results, thickened enzymatically modified isoquercitrin by incorporating a thickening polysaccharide increases the salivation-promoting effect (salivation-increasing effect) of the enzymatically modified isoquercitrin. On the other hand, this enhancement effect on the salivation-promoting effect (salivation-increasing effect) by incorporating a thickening polysaccharide was not observed in quercetin itself or αG rutin, which is also a quercetin glycoside like enzymatically modified isoquercitrin; and this effect was thus found to be specific to enzymatically modified isoquercitrin.

The above results of Experimental Examples 1 to 2 show that when a composition for intraoral use or a composition for oral intake that comprises enzymatically modified isoquercitrin and that is thickened by further incorporating a thickening polysaccharide or the like is ingested as a salivator from the mouth, the amount of saliva secretion is further significantly increased. The results also show that the additive for a composition for intraoral use or the additive for a composition for oral intake according to the present invention is suitable as an additive for preparing a thickened composition for intraoral use or oral intake, or as a swallowing-assisting agent.

Experimental Example 3

(1) Preparation of Test Samples

Various materials in the amounts shown in the formulations of Table 4 were powder-mixed and compression-molded (tableted) at a tableting pressure of 5 kN using a desktop tableting machine (produced by Ichihashi Seiki Co., Ltd.) to prepare enzymatically modified isoquercitrin-containing tablets weighing 1.5 g per tablet (tablet size: 18 mmΦ).

(2) Evaluation of Salivation-Promoting Effect and Results Thereof

The salivation-promoting effect of each test sample prepared above was evaluated in the same manner as in Experimental Example 1 (the panelists were also the same).

TABLE 4

| | | (mass %) |
|---|---|---|
| | Comparative Example | Example |
| Sorbitol | 97.1 | 97 |
| High-sweetness sweetener preparation* | 0.15 | 0.15 |
| Powdery flavor | 0.75 | 0.75 |
| Enzymatically modified isoquercitrin preparation** (α-glucosyl isoquercitrin content (in terms of rutin)) | — | 0.1 (0.01) |
| Sucrose fatty acid ester | 2 | 2 |
| Total | 100 | 100 |

*High-sweetness sweetener preparation: "San Sweet ® SA-8020" (containing 24 mass % sucralose, 18 mass % acesulfame potassium, and 58 mass % reduced palatinose), produced by San-Ei Gen F.F.I., Inc.
**Enzymatically modified isoquercitrin preparation: "San Emiq ® No. 1" (containing 10 mass % α-glucosyl isoquercitrin (in terms of rutin), and further containing dextrin as another component), produced by San-Ei Gen F.F.I. Inc.

(3) Evaluation Results

The average of 3 panelists was shown as numerical values standardized by setting the amount of saliva secretion obtained by using the blank (water) as 1, and the amounts of saliva secretion were evaluated. The value obtained by subtracting the amount of saliva secretion (standardized with water) obtained in the Comparative Example from the amount of saliva secretion (standardized with water) obtained in the Example was 1.52. The administration or intake of tablets containing enzymatically modified isoquercitrin significantly increases the amount of saliva secretion, as compared with the administration or intake of tablets not containing enzymatically modified isoquercitrin.

Example 4: Salivation-Promoting Effect of Sol Compositions for Intraoral Use or Oral Intake (No. 1)

(1) Preparation of Test Samples

The additives for compositions for intraoral use or oral intake containing enzymatically modified isoquercitrin and a thickening polysaccharide in the proportions shown in Table 1 were dissolved in water (20° C.) to prepare sol compositions for intraoral use or oral intake (Test samples 4-1 to 4-5). The viscosity (shear rate: 100 s$^{-1}$) was measured at a product temperature of 20° C. under standard atmospheric pressure conditions. As a control, enzymatically modified isoquercitrin was dissolved in water (20° C.) in the proportion shown in Table 5 to prepare a composition for intraoral use or oral intake (Control sample 4). The viscosity (shear rate: 100 s$^{-1}$) was measured at a product temperature of 20° C. under standard atmospheric pressure conditions. Xanthan gum (produced by San-Ei Gen F.F.I., Inc.) was used as the thickening polysaccharide. "SAN EMIQ® No. 1," which is an enzymatically modified isoquercitrin preparation produced by San-Ei Gen F.F.I., Inc., was used as the enzymatically modified isoquercitrin. The enzymatically modified isoquercitrin tablet contains enzymatically modified isoquercitrin in a proportion of 10 mass % in terms of α-glucosyl isoquercitrin (as rutin [$C_{27}H_{30}O_{16}$]), and further contains dextrin as another component.

The viscosity of the control sample and test samples at a shear rate of 100 s$^{-1}$ was measured using an ARES-LS1 fluid rheometer (jig: 50 mm in diameter, with cone-and-plate geometry, made of resin, 0.05 mm in gap) (produced by TA Instruments) at a sample temperature of 20° C. under standard atmospheric pressure conditions.

The content of enzymatically modified isoquercitrin contained in Control sample 4 and Test samples 4-1 to 4-5 was 150 μM as the α-glucosyl isoquercitrin content in terms of rutin. The content of enzymatically modified isoquercitrin in terms of rutin can be determined according to the quantification method described on the "Enzymatically Modified Isoquercitrin" page in the Specifications and Standards for Food Additives, 8th Edition (The Ministry of Health, Labour and Welfare, Japan) as described above. For example, when the α-glucosyl isoquercitrin content (as rutin ($C_{27}H_{30}O_{16}$)) of an enzymatically modified isoquercitrin preparation (sample A) is 10 mass %, 6100 g (610×(100/10)=6100) of the enzymatically modified isoquercitrin preparation (sample A) (610 is the molecular weight of rutin) correspond to 1 mol of the enzymatically modified isoquercitrin. Accordingly, in the above case, to achieve a molarity of the enzymatically modified isoquercitrin in an aqueous solution of 150 μM (150×10$^{-6}$ mol/L), 0.915 g (6100 g/mol×150×10$^{-6}$ mol) of the enzymatically modified isoquercitrin preparation (sample A) must be dissolved (or dispersed) in 1 L of water.

(2) Measurement of Salivation-Promoting Effect

Using 3 healthy subjects with no salivation abnormalities (subjects A to C: average age: 31.3 years old) as panels, the salivation-promoting effects of the compositions for intraoral use or oral intake (Control sample 4 and Test samples 4-1 to 4-5) and 20° C. water (blank) were evaluated by the method described below.

(a) 15 g of each sample (blank (water), Control sample 4, or Test samples 4-1 to 4-5) is placed in the mouth and retained for 5 seconds, and then swallowed at one time.

(b) After swallowing and after a lapse of 5 seconds, absorbent cotton with a size of 3.75 cm×3.75 cm is placed under the tongue, and retained for 2 minutes. The weight of the absorbent cotton is measured in advance.

(c) After 2 minutes, the absorbent cotton is recovered, and the weight is measured.

(d) From the weight change of the absorbent cotton before and after being placed under the tongue, the amount of saliva secretion by intake of each sample (blank (water), Control sample 4, or Test samples 4-1 to 4-5) was calculated.

TABLE 5

| | Control | Test sample | | | | | (mass %) |
|---|---|---|---|---|---|---|---|
| | sample 4 | 4-1 | 4-2 | 4-3 | 4-4 | 4-5 | |
| Enzymatically modified isoquercitrin preparation* (α-glucosyl isoquercitrin (content in terms of rutin (mass %)**) | 0.0915 (0.00915) | 0.0915 (0.00915) | 0.0915 (0.00915) | 0.0915 (0.00915) | 0.0915 (0.00915) | 0.0915 (0.00915) | |
| Xanthan gum (XG) | — | 0.04 | 0.10 | 0.50 | 1.00 | 2.80 | |
| Water | Balance | Balance | Balance | Balance | Balance | Balance | |
| Total | 100 | 100 | 100 | 100 | 100 | 100 | |
| Proportion of XG per part by mass of α-glucosyl isoquercitrin (content in terms of rutin) (parts by mass) | 0 | 4.4 | 10.9 | 54.6 | 109.3 | 306 | |
| Shear viscosity at a shear rate of 100 s$^{-1}$ (mPa · s) | 1.23 | 9.05 | 19.12 | 61.96 | 95.76 | 364.82 | |

*Enzymatically modified isoquercitrin preparation: "San Emiq ® No. 1," produced by San-Ei Gen F.F.I., Inc.
**Proportion (mass %) of α-glucosyl isoquercitrin (in terms of rutin) in the sample (100 mass %)

Figure 3:
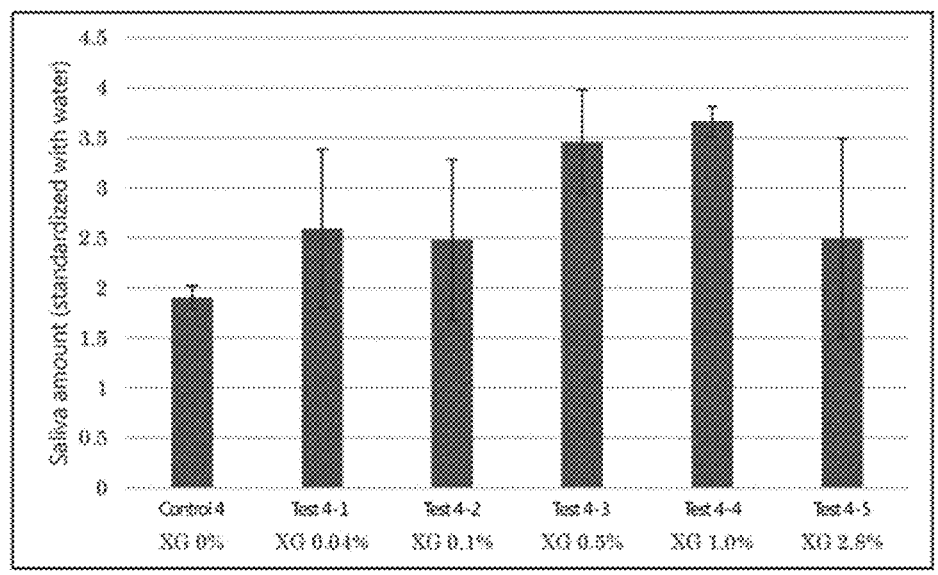
FIG. 3 is a graph showing salivation-promoting effects of sol compositions for intraoral use or oral intake in Experimental Example 4 (Control sample 4, and Test samples 4-1 to 4-5). The xanthan gum (XG) content of each composition for intraoral use or oral intake (mass %) is also shown on the abscissa. The amount of saliva secreted is shown as a relative value, with the amount of saliva secreted by intake of water being set as 1.

Table 6 and FIG. 3 show the results. To eliminate the individual difference in the amount of saliva secretion, Table 6 and FIG. 3 show numerical values (relative values) standardized by setting the average of saliva secretion amount in each subject determined by using water (blank) as 1.

TABLE 6

| | Proportion of XG per part by mass of α-glucosyl isoquercitrin (in terms of rutin) (parts by mass) (α-glucosyl isoquercitrin (as rutin):XG = 1:x) (mass ratio) | Shear viscosity at a shear rate of 100 s$^{-1}$ (mPa · s) | Average of saliva secretion amount* |
|---|---|---|---|
| Water (blank) | — | | 1.00 |
| Control sample 4 | — | | 1.91 |
| Test sample 4-1 | 1:4.4 | 9.05 | 2.59 |
| Test sample 4-2 | 1:10.9 | 19.12 | 2.48 |
| Test sample 4-3 | 1:54.6 | 61.96 | 3.46 |
| Test sample 4-4 | 1:109.3 | 95.76 | 3.66 |
| Test sample 4-5 | 1:306 | 364.82 | 2.50 |

*The average of saliva secretion amount is a relative value with the saliva secretion amount (the average) obtained by intake of the blank (water) being set as 1.

As shown in Table 6, when the compositions for intraoral use or oral intake (Test Samples 4-1 to 4-5) containing an additive for compositions for intraoral use or oral intake, which contained both enzymatically modified isoquercitrin and a thickening polysaccharide (xanthan gum was used in this experiment), are ingested, the amount of saliva secretion increased in all of the subjects, as compared with intake of the blank (water). These compositions for intraoral use or oral intake had no taste or odor. It is thus expected that when the additives for oral compositions (Examples 4-1 to 4-5) used to prepare the above Test samples 4-1 to 4-5 are used, salivation-promoting effects can be imparted to compositions for intraoral use or oral intake, without adversely affecting the flavor of the compositions for intraoral use or oral intake to which the additives are applied.

Control sample 4 not containing a thickening polysaccharide increased the amount of saliva secretion as compared with water (blank). However, the increase in the saliva secretion amount achieved by Control sample 4 was small as compared with that achieved by Test samples 4-1 to 4-5, and Control sample 4 exhibited a lower salivation-promoting effect.

The above results show that a thickening polysaccharide (xanthan gum) itself, when used alone, does not have a salivation-promoting effect; however, when the thickening polysaccharide is used with enzymatically modified isoquercitrin, the salivation-promoting effect of the enzymatically modified isoquercitrin is enhanced.

Example 5: Evaluation of Salivation-Promoting Effect of Sol Compositions for Intraoral Use or Oral Intake (No. 2)

(1) Preparation of Test Samples

Additives for compositions for intraoral use or oral intake containing enzymatically modified isoquercitrin and a thickening polysaccharide in the proportions shown in Table 7 were dissolved in water (20° C.) to prepare sol compositions for intraoral use or oral intake (Test Samples 5-1 to 5-5). Xanthan gum (produced by San-Ei Gen F.F.I., Inc.) was used as the thickening polysaccharide. "San Emiq® No. 1," which is an enzymatically modified isoquercitrin preparation produced by San-Ei Gen F.F.I., Inc., was used as the enzymatically modified isoquercitrin.

TABLE 7

| | Test sample | | | | | (mass %) |
|---|---|---|---|---|---|---|
| | 5-1 | 5-2 | 5-3 | 5-4 | 5-5 | |
| Enzymatically modified isoquercitrin preparation* (α-glucosyl isoquercitrin content (in terms of rutin): mass %**) | 0.0153 (0.00153) | 0.0458 (0.00458) | 0.0915 (0.00915) | 0.4575 (0.04575) | 2.2875 (0.22875) | |
| α-Glucosyl isoquercitrin content (in terms of rutin)* (molarity) | 25 μM | 75 μM | 150 μM | 750 μM | 3750 μM | |
| Xanthan gum (XG) | 0.10 | 0.10 | 0.10 | 0.10 | 0.10 | |
| Water | Balance | Balance | Balance | Balance | Balance | |
| Total | 100 | 100 | 100 | 100 | 100 | |
| Proportion of XG per part by mass of α-glucosyl isoquercitrin (in terms of rutin) (parts by mass) | 65.4 | 21.8 | 10.9 | 2.2 | 0.4 | |

*Enzymatically modified isoquercitrin preparation: "San Emiq ® No. 1," produced by San-Ei Gen F.F.I., Inc.
**Proportion (mass %) of α-glucosyl isoquercitrin (in terms of rutin) in the test sample (100 mass %)

(2) Measurement of Salivation-Promoting Effect

Using 3 healthy subjects with no salivation abnormalities (subjects A to C: average age: 31.3 years old) as panelists, the salivation-promoting effect of compositions for intraoral use or oral intake (Test samples 5-1 to 5-5) and water (blank) (all 20° C.) were evaluated in the same manner as in Experimental Example 4.

Figure 4:
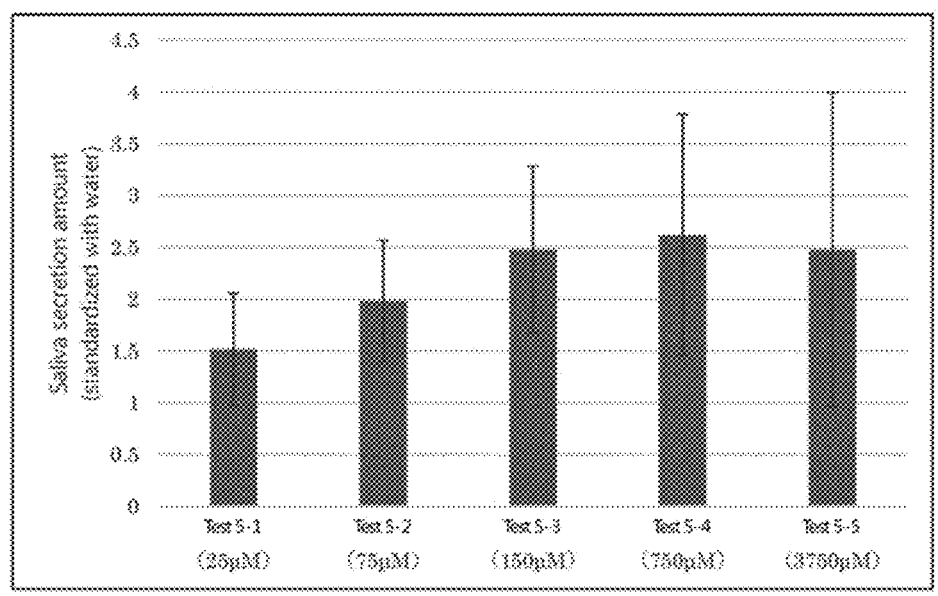
FIG. 4 is a graph showing the salivation-promoting effects of sol compositions for intraoral use or oral intake in Experimental Example 5 (Test samples 5-1 to 5-5). The molarity (µM) of the content of enzymatically modified isoquercitrin in each composition for intraoral use or oral intake in terms of rutin (the content in terms of rutin) is also shown on the abscissa. The amount of saliva secreted is shown as a relative value, with the amount of saliva secreted by intake of water being defined as 1.

Table 8 and FIG. 4 show the results. To eliminate the individual difference in the amount of saliva secretion, Table 8 and FIG. 4 show numerical values (relative values) standardized by setting the average of the saliva secretion amount in each subject determined by using water (blank) as 1.

TABLE 8

| | Molar concentration of α-glucosyl isoquercitrin content (in terms of rutin) | α-Glucosyl isoquercitrin (in terms of rutin):XG = 1:x (mass ratio) | Average of saliva secretion amount* |
|---|---|---|---|
| Water (blank) | — | — | 1.00 |
| Test sample 5-1 | 25 μM | 1:65.4 | 1.52 |
| Test sample 5-2 | 75 μM | 1:21.8 | 1.98 |
| Test sample 5-3 | 150 μM | 1:10.9 | 2.48 |
| Test sample 5-4 | 750 μM | 1:2.2 | 2.62 |
| Test sample 5-5 | 3750 μM | 1:0.4 | 2.48 |

*The average of saliva secretion amount is a relative value with the saliva secretion amount (the average) obtained by intake of the blank (water) being set as 1.

As shown in Table 8, intake of the compositions for intraoral use or oral intake (Test Samples 5-1 to 5-5), which contained an additive for compositions for intraoral use or oral intake containing both enzymatically modified isoquercitrin and a thickening polysaccharide (xanthan gum), increased the amount of saliva secretion in all of the subjects, as compared with intake of the blank (water); and a salivation-promoting effect was observed. These compositions for intraoral use or oral intake had no taste or odor. Incorporating Test samples 5-1 to 5-5 (additives for compositions for oral intake) into compositions for intraoral use or oral intake is thus expected to impart salivation-promoting effects to the compositions for intraoral use or oral intake.

The above results show that when a thickening polysaccharide (xanthan gum) is used with enzymatically modified isoquercitrin, the salivation-promoting effect of the enzymatically modified isoquercitrin increases in a manner dependent on the content of enzymatically modified isoquercitrin used.

Example 6: Salivation-Promoting Effect of Gel Compositions for Intraoral Use or Oral Intake (No. 1)

The additives for compositions for intraoral use or oral intake containing enzymatically modified isoquercitrin and a thickening polysaccharide in the proportions shown in Table 9 were dissolved in water (20° C.) to prepare gel compositions for intraoral use or oral intake, and their salivation-promoting effects were evaluated.

(1) Preparation of Control Samples and Test Samples

The gel compositions for intraoral use or oral intake were prepared following the procedures described below.
1. Among the components shown in Table 9, components (1) to (4) are mixed.
2. The obtained powder mixture is added to ion-exchange water (6), heated to 90° C., and dissolved while stirring at 1300 rpm for 10 minutes.
3. Component (5) is added to the aqueous solution of components (1) to (4), and the weight is corrected with ion-exchange water (6), if necessary.
4. The aqueous solution of (1) to (6) is placed in a resin container having a multilayer structure including an oxygen barrier layer (Lamicon Cup, produced by Toyo Seikan Co., Ltd.), and the container is sealed.
5. The solution is sterilized (85° C., for 30 minutes).
6. The container is cooled to 8° C. to gel the solution, thus obtaining a gel composition for intraoral use or oral intake.
7. The composition is preserved in a 5° C. refrigerator.

TABLE 9

| | Control Sample | | | | | Test Sample | | | | | (mass %) |
|---|---|---|---|---|---|---|---|---|---|---|---|
| | 6-1 | 6-2 | 6-3 | 6-4 | 6-5 | 6-1 | 6-2 | 6-3 | 6-4 | 6-5 | |
| (1) Granulated sugar | 10 | 10 | 10 | 10 | 10 | 10 | 10 | 10 | 10 | 10 | |
| (2) Deacylated gellan gum | 0.03 | 0.25 | 3 | 0.48 | 0.25 | 0.03 | 0.25 | 3 | 0.48 | 0.25 | |
| (3) Highly acylated gellan gum | — | — | — | 0.12 | 0.25 | — | — | — | 0.12 | 0.25 | |
| (4) Enzymatically modified isoquercitrin preparation* (α-glucoside isoquercitrin (in terms of rutin) (mass %)**) | (—) | (—) | (—) | (—) | (—) | 0.0915 (0.00915) | 0.0915 (0.00915) | 0.0915 (0.00915) | 0.0915 (0.00915) | 0.0915 (0.00915) | |
| (5) Calcium lactate | 0.1 | 0.25 | 0.1 | 0.1 | 0.1 | 0.1 | 0.25 | 0.1 | 0.1 | 0.1 | |
| (6) Water | Balance | Balance | Balance | Balance | Balance | Balance | Balance | Balance | Balance | Balance | |
| Total | 100 | 100 | 100 | 100 | 100 | 100 | 100 | 100 | 100 | 100 | |

*Enzymatically modified isoquercitrin preparation: "San Emiq ® No. 1" (containing 10 mass % of enzymatically modified isoquercitrin (in terms of rutin), and further containing dextrin as another component), produced by San-Ei Gen F.F.I., Inc.
**Proportion of α-glucosyl isoquercitrin (in terms of rutin) in the test sample (100 mass %) (mass %)
Test samples 6-1 to 6-5 contain enzymatically modified isoquercitrin as α-glucosyl isoquercitrin in a molarity (in terms of rutin) of 150 μM.

(2) Measurement of Fracture Strain and Hardness of Control Samples and Test Samples (Compositions for Intraoral Use or Oral Intake)

(2-1) Measurement of Fracture Strain

The aqueous solutions of components (1) to (6) of control samples and test samples shown in Table 9 were poured into glass tubular containers (inner diameter: 20 mm, height: 10 mm, thickness: 1.5 mm), and cooled in an 8° C. water tank for 2 hours to solidify the solutions. The containers were then allowed to stand at 5° C. for 15 hours to prepare gel compositions for intraoral use or oral intake having a cylindrical shape (diameter: 20 mm, height: 10 mm) (Control samples 6-1 to 6-5 and Test samples 6-1 to 6-5).

The fracture strain of the gel compositions for intraoral use or oral intake having a cylindrical shape (diameter: 20 mm, height: 10 mm) prepared above were measured following the procedures described below using a texture analyzer (TA-XT-2i (produced by Stable Micro Systems) texture analyzer, probe: P/50 (φ50 mm)). For the measurement, the control samples or test samples were adjusted to a product temperature of 20° C.
(a) Using a jig with a diameter of 100 mm, the control samples or test samples were compressed at a rate of 10 mm/s (start position: 20 mm, clearance: 1 mm).
(b) The yield point of the "load-strain curve" obtained by compression (point at which stress rise is mitigated: peak or inflection point) is defined as the fracture point. The fracture point of the control samples and test samples was determined according to the following formula.

$$\text{Fracture strain} = A/B \qquad [\text{Math. 3}]$$

A: Distance (mm) from the point where the jig first comes into contact with the test sample (the upper surface of the test sample) to the point where the sample is broken by being compressed with the jig (point of fracture).
B: Height of the test sample (=10 mm)
Table 10 shows the results. The values shown in the table are the average of the values measured 3 times by using each of the control samples and test samples.

TABLE 10

|  | Control Sample | | | | | Test Sample | | | | | (mass %) |
| --- | --- | --- | --- | --- | --- | --- | --- | --- | --- | --- |
|  | 6-1 | 6-2 | 6-3 | 6-4 | 6-5 | 6-1 | 6-2 | 6-3 | 6-4 | 6-5 |
| Fracture strain | 0.341 | 0.408 | 0.491 | 0.585 | 0.736 | 0.327 | 0.393 | 0.490 | 0.589 | 0.727 |

(2-2) Measurement of Hardness

Aqueous solutions of the control samples and test samples (1) to (6) shown in Table 9 were poured into stainless steel containers having a cylindrical shape (inner diameter: 40 mm, height: 15 mm), and cooled in an 8° C. water tank for 2 hours to solidify the solutions. The containers were then allowed to stand at 5° C. for 15 hours to obtain gel compositions for intraoral use or oral intake contained in the container having a diameter of 40 mm and a height of 15 mm (control samples 6-1 to 6-5 and test samples 6-1 to 6-5).

The hardness (N/m$^2$) of the gel compositions for intraoral use or oral intake having a cylindrical shape (inner diameter: 40 mm, height: 15 mm) was measured using a texture analyzer (TA-XT-2i (produced by Stable Micro Systems) texture analyzer, probe: P/20 (φ20 mm)). Specifically, using a resin plunger with a diameter of 20 mm and a height of 8 mm, compression measurement was performed twice at a compression rate of 10 mm/s and with a clearance of 5 mm. The maximum stress in the first compression is defined as "hardness" (N/m$^2$). For the measurement, the control samples and test samples were adjusted to a product temperature of 20° C.
Table 11 shows the results.

(3) Evaluation of Salivation-Promoting Effect of Control Samples and Test Samples (Compositions for Intraoral Use or Oral Intake)

Using 3 healthy subjects with no salivation abnormalities (subjects A to C; average age: 31.3 years old) as panelists, salivation-promoting effects of the compositions for intraoral use or oral intake (Control samples 6-1 to 6-5, Test samples 6-1 to 6-5, product temperature: 20° C.) and 20° C. water (blank) were evaluated by the method described below.
(a) 10 g of each sample (Control samples 6-1 to 6-5, Test samples 6-1 to 6-5) is placed in the mouth and freely chewed for 20 seconds, and then swallowed at one time. 10 g of water is placed in the mouth and retained in the mouth for 20 seconds, and then swallowed at one time.
(b) After swallowing and after a lapse of 5 seconds, absorbent cotton with a size of 3.75 cm×3.75 cm×4 mm is placed under the tongue, and retained for 2 minutes. The weight of the absorbent cotton is measured in advance.
(c) After 2 minutes, the absorbent cotton is recovered, and the weight is measured.
(d) From the weight change of the absorbent cotton before and after being placed under the tongue, the amount of saliva secretion by intake of each sample (blank (water), Control samples 6-1 to 6-5, Test samples 6-1 to 6-5) was calculated.

Figure 5:
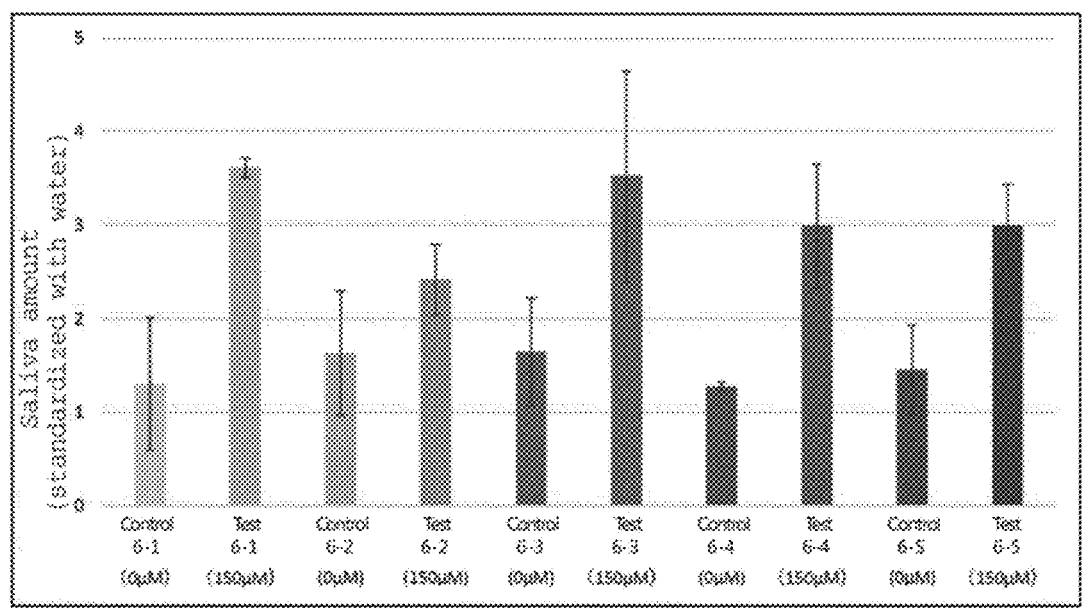
FIG. 5 shows a graph showing the salivation-promoting effect of gel compositions for intraoral use or oral intake in Experimental Example 6 (Control samples 6-1 to 6-5, and Test samples 6-1 to 6-5). The amount of saliva secreted is a relative value, with the amount of saliva secreted by intake of water being defined as 1.

Table 12 and FIG. 5 show the results. Table 12 shows the amount of saliva secretion as well as the fracture strain and hardness. To eliminate the individual difference in the amount of saliva secretion, Table 12 and FIG. 5 show numerical values (relative values) standardized by setting the average of the saliva secretion amount in each subject determined by using water (blank) as 1.

TABLE 12

|  | Fracture strain | Hardness (N/m$^2$) | Average of saliva secretion amount* |
| --- | --- | --- | --- |
| Control Sample 6-1 (not containing enzymatically modified isoquercitrin preparation) | 0.341 | 634 | 1.30 |
| Control Sample 6-2 (not containing enzymatically modified isoquercitrin preparation) | 0.408 | 40,129 | 1.63 |

TABLE 11

|  | Control Sample | | | | | Test Sample | | | | | (mass %) |
| --- | --- | --- | --- | --- | --- | --- | --- | --- | --- | --- |
|  | 6-1 | 6-2 | 6-3 | 6-4 | 6-5 | 6-1 | 6-2 | 6-3 | 6-4 | 6-5 |
| Hardness (N/m$^2$) | 634 | 40,129 | 388,694 | 28,074 | 22,413 | 712 | 36,937 | 377,503 | 29,045 | 22,215 |

TABLE 12-continued

| | Fracture strain | Hardness (N/m²) | Average of saliva secretion amount* |
|---|---|---|---|
| Control Sample 6-3 (not containing enzymatically modified isoquercitrin preparation) | 0.491 | 388,694 | 1.65 |
| Control Sample 6-4 (not containing enzymatically modified isoquercitrin preparation) | 0.585 | 28,074 | 1.28 |
| Control Sample 6-5 (not containing enzymatically modified isoquercitrin preparation) | 0.736 | 22,413 | 1.46 |
| Test Sample 6-1 (containing 150 µM enzymatically modified isoquercitrin preparation) | 0.327 | 712 | 3.61 |
| Test Sample 6-2 (containing 150 µM enzymatically modified isoquercitrin preparation) | 0.393 | 36,937 | 2.42 |
| Test Sample 6-3 (containing 150 µM enzymatically modified isoquercitrin preparation) | 0.490 | 377,503 | 3.52 |
| Test Sample 6-4 (containing 150 µM enzymatically modified isoquercitrin preparation) | 0.589 | 29,045 | 2.99 |
| Test Sample 6-5 (containing 150 µM enzymatically modified isoquercitrin preparation) | 0.727 | 22,215 | 2.99 |

*The average of saliva secretion amount is a relative value with the saliva secretion amount (the average) by intake of the blank (water) being set as 1.

As shown in the above table, a clear difference in the amount of saliva secretion was observed between the gel compositions for intraoral use or oral intake containing enzymatically modified isoquercitrin (test samples 6-1 to 6-5), and the gel compositions for intraoral use or oral intake not containing enzymatically modified isoquercitrin (control samples 6-1 to 6-5). The results also confirmed that the amount of saliva secretion is significantly promoted and increased by chewing the gel compositions for intraoral use or oral intake containing enzymatically modified isoquercitrin in the oral cavity, or swallowing the compositions.

Experimental Example 7: Salivation-Promoting Effect of Gel Compositions for Intraoral Use or Oral Intake (No. 2)

The additive for a composition for intraoral use or oral intake containing enzymatically modified isoquercitrin and a thickening polysaccharide in a proportion shown in Table 13 was dissolved in water (20° C.) to prepare a gel composition for intraoral use or oral intake. The salivation-promoting effect of the gel composition for intraoral use or oral intake was evaluated following the method disclosed in Experimental Example 6.

(1) Preparation of Control Sample and Test Samples

Gel compositions for intraoral use or oral intake were prepared following the procedures described below.

1. Among the components shown in Table 13, components (1) to (3) are powder-mixed.
2. The powder mixture is added to ion-exchange water (5), heated to 90° C., and dissolved while stirring at 1300 rpm for 10 minutes.
3. Component (4) is added to the aqueous solution and the weight is corrected with ion-exchange water (5), if necessary.
4. The aqueous solution of components (1) to (5) prepared above is placed in a resin container having a multilayer structure including an oxygen barrier layer (Lamicon Cup, produced by Toyo Seikan Co., Ltd.), and the container is sealed.
5. The solution is sterilized (85° C., for 30 minutes).
6. The container is cooled to 8° C. to gel the solution, thus producing a gel composition for intraoral use or oral intake.
7. The composition is preserved in a 5° C. refrigerator.

The composition for intraoral use or oral intake thus prepared had a fracture strain of 0.511 to 0.526, and a hardness of 41,528 to 54,170 N/m².

TABLE 13

| | Control sample 7 | Test sample 7-1 | 7-2 | 7-3 | 7-4 | 7-5 | 7-6 |
|---|---|---|---|---|---|---|---|
| (1) Granulated sugar | 10 | 10 | 10 | 10 | 10 | 10 | 10 |
| (2) Deacylated gellan gum | 0.55 | 0.55 | 0.55 | 0.55 | 0.55 | 0.55 | 0.55 |
| (3) Enzymatically modified isoquercitrin preparation* (as α-glucoside isoquercitrin (in terms of rutin) (mass %)*) | 0 (0) | 0.00612 (0.000612) | 0.0153 (0.00153) | 0.0458 (0.00458) | 0.0915 (0.00915) | 0.4575 (0.04575) | 2.2875 (0.22875) |
| (Concentration of α-glucoside isoquercitrin in terms of rutin) | (0 µM) | (10 µM) | (25 µM) | (75 µM) | (150 µM) | (750 µM) | (3750 µM) |
| (4) Calcium lactate | 0.1 | 0.1 | 0.1 | 0.1 | 0.1 | 0.1 | 0.1 |
| (5) Water | Balance | Balance | Balance | Balance | Balance | Balance | Balance |
| Total | 100 | 100 | 100 | 100 | 100 | 100 | 100 |

*Enzymatically modified isoquercitrin preparation: "San Emiq ® No. 1" (containing 10 mass % of enzymatically modified isoquercitrin (in terms of rutin) and further containing dextrin as another component), produced by San-Ei Gen F.F.I., Inc.
*Proportion of α-glucosyl isoquercitrin (in terms of rutin) in the test sample (100 mass %) (mass %)

(2) Evaluation of Salivation-Promoting Effect of Test Samples (Compositions for Intraoral Use or Oral Intake)

Using 3 healthy subjects with no salivation abnormalities (subjects A to C: average age: 31.3 years old) as panelists, the salivation-promoting effects of the compositions for intraoral use or oral intake (Control sample 7, Test samples 7-1 to 7-6, product temperature: 20° C.) and 20° C. water (blank) were evaluated by the method described below.

(a) After 10 g of each sample (Control sample 7 and Test samples 7-1 to 7-6) is placed in the mouth and freely chewed for 20 seconds, the sample is swallowed at one time. After 10 g of water is placed in the mouth and retained in the mouth for 20 seconds, the water is swallowed at one time.
(b) After swallowing and after a lapse of 5 seconds, absorbent cotton with a size of 3.75 cm×3.75 cm×4 mm is placed under the tongue and retained for 2 minutes. The weight of the absorbent cotton is measured in advance.
(c) After 2 minutes, the absorbent cotton is collected and the weight is measured.
(d) From the weight change of the absorbent cotton before and after being placed under the tongue, the amount of saliva secretion by intake of each sample (blank (water), Control sample 7, Test samples 7-1 to 7-6) was calculated.

Figure 6:
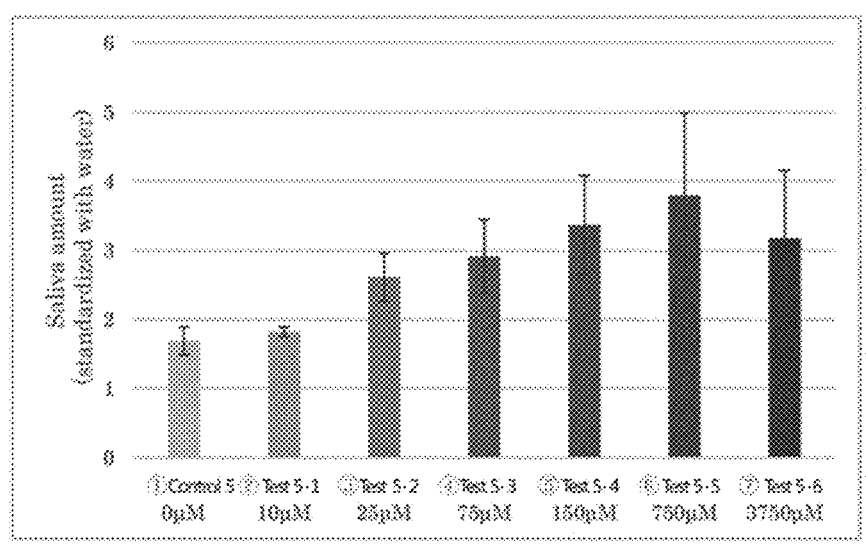
FIG. 6 is a graph showing the saliva secretion-promoting effects of gel compositions for intraoral use or oral intake in Experimental Example 7 (Control sample 7, and Test samples 7-1 to 7-5). The molarity (µM) of the content of enzymatically modified isoquercitrin in each composition for intraoral use or oral intake in terms of rutin (the content in terms of rutin) is also shown on the abscissa. The amount of saliva secreted is a relative value, with the amount of saliva secreted by intake of water being defined as 1.

Table 14 and FIG. 6 show the results. To eliminate the individual difference in the amount of saliva secretion, Table 14 and FIG. 6 show numerical values (relative values) standardized by setting the average of the saliva secretion amount in each subject determined by using water (blank) as 1.

TABLE 14

| Sample (concentration of α-glucosyl isoquercitrin, in terms of rutin) | Fracture strain | Hardness ($N/m^2$) | Average of saliva secretion amount* |
|---|---|---|---|
| Control sample 7 (0 μM) | 0.526 | 41528 | 1.70 |
| Test sample 7-1 (10 μM) | 0.523 | 50679 | 1.83 |
| Test sample 7-2 (25 μM) | 0.511 | 42880 | 2.61 |
| Test sample 7-3 (75 μM) | 0.517 | 46429 | 2.92 |
| Test sample 7-4 (150 μM) | 0.521 | 54170 | 3.37 |
| Test sample 7-5 (750 μM) | 0.513 | 49575 | 3.78 |
| Test sample 7-6 (3750 μM) | 0.518 | 49914 | 3.18 |

*The average of saliva secretion amount is a relative value with the saliva secretion amount (the average) obtained by intake of a blank sample (water) being set as 1.

As shown in Table 14, although Control sample 7 in the form of a gel not containing enzymatically modified isoquercitrin also increased the amount of saliva secretion, a combination of enzymatically modified isoquercitrin with a thickening polysaccharide (Test samples 7-1 to 7-6) was confirmed to increase the amount of saliva secretion more significantly than the control sample. The results further confirmed that the effect of increasing the amount of saliva secretion is dependent on the amount of enzymatically modified isoquercitrin incorporated (dose-dependent).

The above results of Experimental Examples 6 to 7 show that when gel compositions for intraoral use or oral intake that comprise a salivator comprising a thickening polysaccharide in addition to enzymatically modified isoquercitrin and that have a fracture strain within the range of 0.3 to 0.8 or/and a hardness of 500 to 500,000 $N/m^2$ are orally ingested, saliva secretion significantly increases. The results further show that the additive for compositions for intraoral use or oral intake according to the present invention is suitable as an additive for preparing a gel composition for intraoral use or oral intake having a specific fracture strain or/and hardness as described above.

The invention claimed is:

1. A method of promoting salivation in a person with reduced salivation function, the method comprising applying a salivator to the oral cavity of the person or allowing the person to orally ingest the salivator,
wherein the salivator comprises an enzymatically modified isoquercitrin in an effective amount to provide a salivation-promoting effect, and a thickening polysaccharide,
the enzymatically modified isoquercitrin contains as a main component a mixture of two or more a-glucosyl isoquercitrins represented by the following formula:

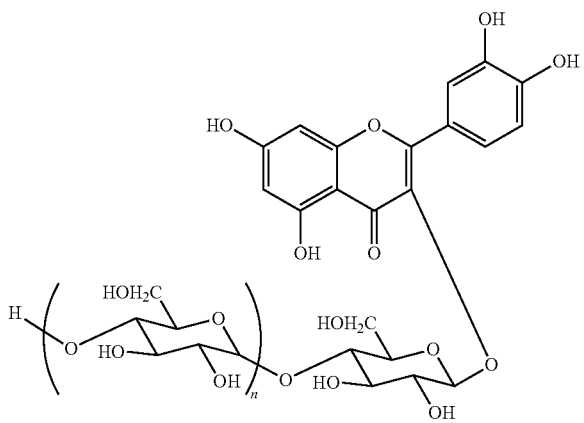

wherein n represents an integer of 0 to 10, and
the effective amount is 0.001 to 0.5 mass % in terms of a-glucosyl isoquercitrin.

2. The method according to claim 1, wherein the amount of the salivator applied to the oral cavity or orally ingested is 0.1 to 250 mg per dose in terms of the enzymatically modified isoquercitrin contained in the salivator.

3. The method according to claim 1, wherein the effective amount is 0.00153 to 0.22875 mass % in terms of a-glucosyl isoquercitrin.

4. The method according to claim 1, wherein the enzymatically modified isoquercitrin contains α-glucosyl isoquercitrin in an amount of 60 mass % or more in terms of rutin.

5. The method according to claim 1, wherein the thickening polysaccharide is at least one member selected from the group consisting of xanthan gum, locust bean gum, guar gum, tara gum, deacylated gellan gum, native gellan gum, pectin, alginate, gelatin, agar, psyllium seed gum, and carrageenan.

6. The method according to claim 1, wherein the content of the thickening polysaccharide is 0.2 to 500 parts by mass per part by mass of the enzymatically modified isoquercitrin in terms of rutin.

7. The method according to claim 1, further comprising an edible metal salt.

8. The method according to claim 7, wherein the edible metal salt is at least one member selected from the group consisting of sodium salts, potassium salts, calcium salts, and magnesium salts.

9. The method according to claim 7, wherein the content of the edible metal salt is 0.1 to 15 mass %.

10. The method according to claim 1, wherein the salivator is in the form of a syrup, health drink, liquid, emulsion, oil, spray, gel, paste, tablet, chewable agent, lozenge, pill, granule, powder, dry syrup, film, or stick-shaped preparation.

11. The method according to claim 1, wherein
the salivator is in a solid form, a paste or liquid form, or a gel form,
the salivator in a solid form contains the thickening polysaccharide in an amount of 1 to 99.9 mass %,
the salivator in a paste or liquid form contains the thickening polysaccharide in an amount of 0.02 to 30 mass %, and the salivator in a gel form contains the thickening polysaccharide in an amount of 0.02 to 10 mass %.

* * * * *